(12) United States Patent
Jones et al.

(10) Patent No.: US 6,274,140 B1
(45) Date of Patent: Aug. 14, 2001

(54) CALCIUM INDEPENDENT CYTOSOLIC PHOSPHOLIPASE A₂/B ENZYMES

(75) Inventors: Simon Jones, Somerville; Jin Tang, Canton, both of MA (US)

(73) Assignee: Genetics Institute, Inc.

( * ) Notice: Subject to any disclaimer, the term of this patent is extended or adjusted under 35 U.S.C. 154(b) by 0 days.

(21) Appl. No.: 09/519,223

(22) Filed: Mar. 6, 2000

Related U.S. Application Data

(60) Continuation of application No. 09/149,988, filed on Sep. 9, 1998, which is a division of application No. 08/555,568, filed on Nov. 8, 1995, now Pat. No. 5,976,854, which is a continuation-in-part of application No. 08/281,193, filed on Jul. 27, 1994, now Pat. No. 5,466,595, which is a continuation-in-part of application No. 08/422,106, filed on Apr. 14, 1995, now Pat. No. 5,589,170, which is a continuation-in-part of application No. 08/422,420, filed on Apr. 14, 1995, now Pat. No. 5,554,511.

(51) Int. Cl.⁷ .............................. A61K 38/46; C12N 9/20; C12N 1/20; C12N 15/00; C07H 21/04

(52) U.S. Cl. .................. 424/94.6; 435/198; 435/252.3; 435/320.1; 435/536; 435/23.2; 435/530; 435/300; 435/350

(58) Field of Search .................. 424/96.6; 435/198; 435/252.3, 320.1; 536/23.2; 530/350, 300

(56) References Cited

U.S. PATENT DOCUMENTS

| | | | |
|---|---|---|---|
| 4,239,780 | 12/1980 | Wallach | 424/330 |
| 4,917,826 | 4/1990 | Johnson et al. | 552/522 |
| 5,279,957 | 1/1994 | Gross | 435/240 |
| 5,322,776 | 6/1994 | Knopf et al. | 435/69 |
| 5,356,787 | 10/1994 | Gross | 435/18 |
| 5,466,595 | 11/1995 | Jones et al. | 435/240 |
| 5,554,511 | 9/1996 | Jones et al. | 435/69 |
| 5,589,170 | * 12/1996 | Jones et al. | 424/94.6 |
| 5,976,854 | 11/1999 | Jones et al. | 435/198 |

OTHER PUBLICATIONS

Aarsman, A.J. et al. "Immunoaffintiy purification, partial sequence, and subcellular localization of rat liver phospholipase A2" *J. Biol. Chem.* 264(17):10008–14 (1989).

Ackermann, E.J. et al., "Ca²⁺–independent cytosolic phospholipase A2 from macrophage–like P388D1 cells. Isolation and characterization" *J. Biol. Chem.* 269:9227 (1994).

Ackermann et al. *FASEB J.* 7(7):1237 (1993).

Angle, M.J. et al. "Selective hydrolysis of ether–containing glycerophospholipids by phospholipase A2 in rabbit lung" *Biochim. Biophys. Acta* 962:234 (1988).

Cao, Y.Z. et al. "The purification and characterization of a phospholipase A in hamster heart cytosol for the hydrolysis of phosphatidylcholine" *J. Biol. Chem.* 262(35):16927–35 (1987).

Clark, J.D. "A novel arachidonic acid–selective cytosolic PLA2 contains a Ca²⁺–dependent translocation domain with homology to PKC and GAP" *Cell* 65:1043–51 (1991).

de Carvalho, M.S. et al. "The 85–kDa, arachidonic acid–specific phospholipase A2 is expressed as an activated phosphoprotein in Sf9 cells" *Arch. Biochem. Biophys.* 306(2):534–40 (1993).

Dennis, E. A. "Diversity of group types, regulation, and function of phospholipase A2" *J. Biol. Chem.* 269(18):13057–60 (1994).

Ford, D.A. et al. "The rapid and reversible activation of a calcium–independnet plasmalogen–selective phospholipase A2 during myocardial ischemia" *J. Clin. Invest.* 88(1):331–35 (1991).

Gassama–Diagne, A. et al. "Substrate specificity of phospholipase B from guinea pig intestine. A glycerol ester lipase with broad specificity" *J. Biol. Chem.* 267(19):13418–24 (1992).

Gassama–Diagne, A. et al., "Purification of a new, calcium–independent, high molecular weight phospholipase A2/lysophosholipase (phospholipase B) from guinea pig intestinal brush–border membrane" *J. Biol. Chem.* 264(16):9470–75 (1989).

Gross, R.W. et al. "Rat and human pancreatic islet cells contain a calcium ion independent phospholipase A2 activity selective for hydrolysis of arachidonate which is stimulated by adenosine triphosphate and is specifically localized to islet beta–cells" *Biochemistry* 32(1):327–36 (1993).

Gross, TCM 2:115 (1991).

Han, J.H. et al. "Isolation of full–length putative rat lysophospholipase cDNA using improved methods for mRNA isolation and cDNA cloning" *Biochemistry* 26:1617–25 (1987).

Hazen, S.L. et al. "Isolation of a human myocardial cytosolic phospholipase A2 isoform. Fast atom bombardment mass spectroscopic and reverse–phase high pressure liquid chromatography identification of choline and ethanolamine glycerophospholipid substrates" *J. Clin. Invest.* 91(6):2513–22 (1993).

Hazen, S.L. et al. "The specific association of a phosfructokinase isoform with myocardial calcium–independent phospholipase A2. Implications for the coordinated regualtion of phospholipolysis and glycolysis" *J. Biol. Chem.* 268(13):9892–9900 (1993).

Hazen, S.L. and Gross, R. W. "Identification and characterization of human myocardial phospholipase A2 from transplant recipients suffering from end–stage ischemic heart disease" *Circulation Res.* 70(3):486–95 (1992).

(List continued on next page.)

Primary Examiner—Ponnathapu Achutamurthy
Assistant Examiner—Tekchand Saidha
(74) Attorney, Agent, or Firm—Lahive & Cockfield, LLP; Amy E. Mandragouras

(57) ABSTRACT

The invention provides a novel calcium-independent cytosolic phospholipase A₂/B enzyme, polynucleotides encoding the enzyme and methods for screening unknown compounds for anti-inflammatory activity mediated by the arachidonic acid cascade.

13 Claims, 7 Drawing Sheets

OTHER PUBLICATIONS

Hazen, S.L. and Gross, R.W. "ATP–dependent regulation of rabbit myocardial cytosolic calcium–independent phospholipase A2" *J. Biol. Chem.* 266(22):14526–34 (1991).

Hazen, S.L. et al. "Sucide inhibition of canine myocardial cytosolic calcium–independent phospholipase A2. Mechanism–based discrimintation between calcium–dependent and–independent phospholipases A2" *J. Biol. Chem.* 266(11):7227–32 (1991).

Hazen, S.L. et al., "Activation of a membrane–associated phospholipase A2 during rabbit myocardial ischemia which is highly selective for plasmalogen substrate" *J. Biol. Chem.* 266(9):5629–33 (1991).

Hazen, S.L. et al. "Puruficàtion and characterization of cytosolic phospholipase A2 activities from canine myocardium and sheep platelets" *Methods Enzymol.* 197:400–11 (1991).

Hazen, S.L. et al. "Purification and characterization of canine myocardial cytosolic phospholipase A2. A calcium–independent phospholipase with absolute f1–2 regiospecificity for diradyl glycerophospholipids" *J. Biol. Chem.* 265(18):10622–30 (1990).

Hirashima, Y. et al., "Identification and purification of calcium–independent phosphlipase A2 from bovine brain cytosol" *J. Neurochem.* 59(2):708–14 (1992).

Kanda, A. et al. "The primary structure of a membrane–associated phospholipase A2 from human spleen" *Biochem. Biophys. Res. Comm.* 163:42 (1989).

Kaufman, Randal J. et al. "Improved vectors for stable expression of foreign genes in mammalian cells by use of the untranslated leader sequence from EMC virus" *Nucleic Acids Res.* 19(16):4485–4490 (1991).

Kaufman, R.J. "Selection and Coamplification of Heterologous Genes in Mammalian Cells" *Methods in Enzymol.* 185:537–66 (1990).

Kramer, R.M. et al. "Structure and properties of a human non–pancreatic phospholipase A2" *J. Biol. Chem.* 264:5768–75 (1989).

Lehman, J.J. et al. "Arachidonic acid release from aortic smooth muscle cells induced by [Arg8] vasopressin is largely mediated by calcium–independent phospholipase A2" *J. Biol. Chem.* 268(28):20713–16 (1993).

Leslie, C. C. et al. "Properties and purification of an arachidonoyl–hydrolyzing phospholipase A2 from a macrophage cell line, RAW 264.7" *Biochim. Biophys. Acta* 963:476–92 (1988).

Loeb, L.A. and Gross, R.W. "Identification and purification of sheep platelet phospholipase A2 isoforms. Activation by physiologic concentrations of calcium ion" *J. Biol. Chem.* 261(23):10467–70 (1986).

Nijssen, J.G. "Identification of a calcium–independent phospholipase A2 in rat lung cytosol and differentiation from acetylhydrolase for 1–alkyl–2–acetyl–sn–glycero–3–phosphocholine (PAF–acether)" *Biochim. Biophys. Acta* 876(3):611–18 (1986).

Pierik, A.J. et al. "Calcium–independent phospholipase A2 in rat tissue cytosols" *Biochim. Biophys. Acta* 962(3):345–53 (1988).

Ramanadham, S. et al. "Characterization of an ATP–stimulatable Ca(2+)–independent phospholipase A2 from clonal insulin–secreting HIT cells and rat pancreatic islets: a possible molecular component of the beta–cell fuel sensor" *Biochemistry* 33(23):7442–52 (1994).

Ramanadham, S. et al. "Inhibition of arachidonate release by secretagogue–stimulated pancreatic islets suppresses both insulin secretion and the rise in beta–cell cytosolic calcium ion concentration" *Biochemistry* 32(1):337–46 (1993).

Ross, M.I. et al. "Phospholipase activities of the P388D1 macrophage–like cell line" *Arch. Biochem. Biophys.* 238(1):247–58 (1985).

Saito, K. et al. "Phospholipase B from *Penicillium notatum*" *Methods of Enzymol.* 197:446–56 (1991).

Seilhamer, J.J. et al. "Cloning and recombinant expression of phospholipase A2 present in rheumatoid arthritic synovial fluid" *J. Biol. Chem.* 264(10):5335–38 (1989).

Sharp, J.D. et al. "Molecular cloning and expression of human $Ca^{2+}$sensitive cytosolic phospholipase A2" *J. Biol. Chem.* 266(23):14850–53 (1991).

Tang, J. et al. "A novel cytosolic calcium–independent phospholipase A2 contains eight ankyrin motifs" *J. Biol. Chem.* 272(13):8567–75 (1997).

Ueda, H. et al. "The presence of $Ca^{2+}$independent phospholipase A1 highly specific for phosphatidylinosital in bovine brain" *Biochem. Biophys. Res. Comm.* 195(3):1272–79 (1993).

Ulevitch, R.J. et al. "Solubilization, purification, and characterization of a membrane–bound phospholipase A2 from the P388D1 macrophage–like cell line" *J. Biol. Chem.* 263(7):3079–85 (1988).

Wolf, R.A. and Gross, R.W. "Identifiction of neutral active phospholipase C which hydrolyzes choline glycerophospholipids and plasmalogen selective phospholipase A2 in canine myocardium" *J. Biol. Chem.* 260(12):7295–7303 (1985).

Yost, R.W. et al. "Yeast mitochondria (*Saccharomyces cerevisiae*) contain $Ca^{2+}$independent phospholipase A1 and A2 activities: effect of respiratory state" *Biochem. International* 24(2):199–208 (1991).

Zupan, L.A. et al. "Structural determinants of haloenol lactone–mediated suicide inhibition of canine myocardial calcium–independent phospholipase A2" *J. Med. Chem.* 36(1):95–100 (1993).

Zupan, L.A. et al. "Cloning and expression of a human 14–3–3 protein mediating phospholipolysis. Identification of an arachidonoly–enzyme intermediate during catalysis" *J. Biol. Chem.* 267(13):870710 (1992).

Zupan, Lori A. et al. "Calcium is sufficient but not necessary for activation of sheep platelet cytosolic phospholipase $A_2$" *FEBS Lett.* 284(1):27–30 (1991).

* cited by examiner 3-1

3-2

CALCIUM INDEPENDENT CYTOSOLIC PHOSPHOLIPASE $A_2$/B ENZYMES

This application is a continuation of application Ser. No. 09/149,988, filed Sep. 9, 1998; which is a divisional of application Ser. No. 08/555,568, filed Nov. 8, 1995 and issued as U.S. Pat. No. 5,976,854; which was a continuation-in-part of the following applications: (1) Ser. No. 08/281,193, filed Jul. 27, 1994 and issued as U.S. Pat. No. 5,466,595; (2) Ser. No. 08/422,106, filed Apr. 14, 1995 and issued as U.S. Pat. No. 5,589,170; and (3) Ser. No. 08/422,420, filed Apr. 14, 1995 and issued as U.S. Pat. No. 5,554,511; all of which are incorporated by reference herein.

The present invention relates to a purified calcium independent cytosolic phospholipase $A_2$/B enzymes which are useful for assaying chemical agents for anti-inflammatory activity.

BACKGROUND OF THE INVENTION

The phospholipase $A_2$ enzymes comprise a widely distributed family of enzymes which catalyze the hydrolysis of the acyl ester bond of glycerophospholipids at the sn-2 position. One kind of phospholipase $A_2$ enzymes, secreted phospholipase $A_2$ or $sPLA_2$, are involved in a number of biological functions, including phospholipid digestion, the toxic activities of numerous venoms, and potential antibacterial activities. A second kind of phospholipase $A_2$ enzymes, the intracellular phospholipase $A_2$ enzymes, also known as cytosolic phospholipase $A_2$ or $cPLA_2$, are active in membrane phospholipid turnover and in regulation of intracellular signalling mediated by the multiple components of the well-known arachidonic acid cascade. One or more $cPLA_2$ enzymes are believed to be responsible for the rate limiting step in the arachidonic acid cascade, namely, release of arachidonic acid from membrane glycerophospholipids. The action of $cPLA_2$ also results in biosynthesis of platelet activating factor (PAF).

The phospholipase B enzymes are a family of enzymes which catalyze the hydrolysis of the acyl ester bond of glycerophospholipids at the sn-1 and sn-2 positions. The mechanism of hydrolysis is unclear but may consist of initial hydrolysis of the sn-2 fatty acid followed by rapid cleavage of the sn-1 substituent, i.e., functionally equivalent to the combination of phospholipase $A_2$ and lysophospholipase (Saito et al., Methods of Enzymol., 1991, 197, 446; Gassama-Diagne et al., J. Biol. Chem., 1989, 264, 9470). Whether these two events occur at the same or two distinct active sites has not been resolved. It is also unknown if these enzymes have a preference for the removal of unsaturated fatty acids, in particular arachidonic acid, at the sn-2 position and accordingly contribute to the arachidonic acid cascade.

Upon release from the membrane, arachidonic acid may be metabolized via the cyclooxygenase pathway to produce the various prostaglandins and thromboxanes, or via the lipoxygenase pathway to produce the various leukotrienes and related compounds. The prostaglandins, leukotrienes and platelet activating factor are well known mediators of various inflammatory states, and numerous anti-inflammatory drugs have been developed which function by inhibiting one or more steps in the arachidonic acid cascade. Use of the present anti-inflammatory drugs which act through inhibition of arachidonic acid cascade steps has been limited by the existence of side effects which may be harmful to various individuals.

A very large industrial effort has been made to identify additional anti-inflammatory drugs which inhibit the arachidonic acid cascade. In general, this industrial effort has employed the secreted phospholipase $A_2$ enzymes in inhibitor screening assays, for example, as disclosed in U.S. Pat. No. 4,917,826. However, because the secreted phospholipase $A_2$ enzymes are extracellular proteins (i.e., not cytosolic) and are not specific for hydrolysis of arachidonic acid, they are presently not believed to participate directly in the arachidonic acid cascade. While some inhibitors of the small secreted phospholipase $A_2$ enzymes have anti-inflammatory action, such as indomethacin, bromphenacyl bromide, mepacrine, and certain butyrophenones as disclosed in U.S. Pat. No. 4,239,780, it is presently believed that inhibitor screening assays should employ cytosolic phospholipase $A_2$ enzymes which directly participate in the arachidonic acid cascade.

An improvement in the search for anti-inflammatory drugs which inhibit the arachidonic acid cascade was developed in commonly assigned U.S. Pat. No. 5,322,776, incorporated herein by reference. In that application, a cytosolic form of phospholipase $A_2$ was identified, isolated, and cloned. Use of the cytosolic form of phospholipase $A_2$ to screen for anti-inflammatory drugs provides a significant improvement in identifying inhibitors of the arachidonic acid cascade. The cytosolic phospholipase $A_2$ disclosed in U.S. Pat. No. 5,322,776 is a 110 kD protein which depends on the presence of elevated levels of calcium inside the cell for its activity. The $cPLA_2$ of U.S. Pat. No. 5,322,776 plays a pivotal role in the production of leukotrienes and prostaglandins initiated by the action of pro-inflammatory cytokines and calcium mobilizing agents. The $cPLA_2$ of U.S. Pat. No. 5,322,776 is activated by phosphorylation on serine residues and increasing levels of intracellular calcium, resulting in translocation of the enzyme from the cytosol to the membrane where arachidonic acid is selectively hydrolyzed from membrane phospholipids.

In addition to the $cPLA_2$ of U.S. Pat. No. 5,322,776, some cells contain calcium independent phospholipase $A_2$/B enzymes. For example, such enzymes have been identified in rat, rabbit, canine and human-heart tissue (Gross, TCM, 1991, 2, 115; Zupan et al., J. Med. Chem., 1993, 36, 95; Hazen et al., J. Clin. Invest., 1993, 91, 2513; Lehman et al., J. Biol. Chem., 1993, 268, 20713; Zupan et al., J. Biol. Chem., 1992, 267, 8707; Hazen et al., J. Biol. Chem., 1991, 266, 14526; Loeb et al., J. Biol. Chem., 1986, 261, 10467; Wolf et al., J. Biol. Chem., 1985, 260, 7295; Hazen et al., Meth. Enzymol., 1991, 197, 400; Hazen et al., J. Biol. Chem., 1990, 265, 10622; Hazen et al., J. Biol. Chem., 1993, 268, 9892; Ford et al., J. Clin. Invest., 1991, 88, 331; Hazen et al., J. Biol. Chem., 1991, 266, 5629; Hazen et al., Circulation Res., 1992, 70, 486; Hazen et al., J. Biol. Chem., 1991, 266, 7227; Zupan et al., FEBS, 1991, 284, 27), as well as rat and human pancreatic islet cells (Ramanadham et al., Biochemistry, 1993, 32, 337; Gross et al., Biochemistry, 1993, 32, 327), in the macrophage-like cell line, $P388D_1$ (Ulevitch et al., J. Biol. Chem., 1988, 263, 3079; Ackermann et al;, J. Biol. Chem., 1994, 269, 9227; Ross et al., Arch. Biochem. Biophys., 1985, 238, 247; Ackermann et al., FASEB Journal, 1993, 7(7), 1237), in various rat tissue cytosols (Nijssen et al., Biochim. Biophys. Acta, 1986, 876, 611; Pierik et al., Biochim. Biophys. Acta, 1988, 962, 345; Aarsman et al., J. Biol. Chem., 1989, 264, 10008), bovine brain (Ueda et al., Biochem. Biophys, Res. Comm., 1993, 195, 1272; Hiroshima et al., J. Neurochem., 1992, 59, 708), in yeast (*Saccharomyces cerevisiae*) mitochondria (Yost et al., Biochem. International, 1991, 24, 199), hamster heart cytosol (Cao et al., J. Biol. Chem., 1987, 262, 16027), rabbit lung microsomes (Angle et al., Biochim. Biophys. Acta, 1988, 962, 234) and guinea pig intestinal brush-border membrane (Gassama-Diagne et al., J. Biol. Chem., 1989, 264, 9470).

It is believed that the calcium independent phospholipase $A_2$/B enzymes may perform important functions in release of arachidonic acid in specific tissues which are characterized by unique membrane phospholipids, by generating lysophospholipid species which are deleterious to membrane integrity or by remodeling of unsaturated species of membrane phospholipids through deacylation/reacylation mechanisms. The activity of such a phospholipase may well be regulated by mechanisms that are different from that of the $cPLA_2$ of U.S. Pat. No. 5,322,776. In addition the activity may be more predominant in certain inflamed tissues over others. Although the enzymatic activity is not dependent on calcium this does not preclude a requirement for calcium in vivo, where the activity may be regulated by the interaction of other protein(s) whose function is dependent upon a calcium flux.

SUMMARY OF THE INVENTION

In certain embodiments, the present invention provides compositions comprising a purified phospholipase enzyme characterized by (a) activity in the absence of calcium; (b) a molecular weight of 86 kD on SDS-PAGE; and (c) the presence of one or more amino acid sequences selected from the group consisting of NPHSGFR (SEQ ID NO:3), XAS-XGLNQVNK (SEQ ID NO:4) (X is preferably N or A), YGASPLHXAK (SEQ ID NO:5) (X is preferably W), DNMEMIK (SEQ ID NO:6), GVYFR (SEQ ID NO:7), MKDEVFR (SEQ ID NO:8), EFGEHTK (SEQ ID NO:9), VMLTGTLSDR (SEQ ID NO:10), XYDAPEVIR (SEQ ID NO:11) (X is preferably N), FNQNINLKPPTQPA (SEQ ID NO:12), XXGAAPTYFRP (SEQ ID NO:13) (X is preferably S), TVFGAK (SEQ ID NO:14), and XWSEM-VGIQYFR (SEQ ID NO:15) (X is preferably A), wherein X represents any amino acid residue.

In other embodiments, the invention provides compositions comprising a purified phospholipase enzyme characterized by (a) activity in the absence of calcium; (b) a molecular weight of 86 kD on SDS-PAGE; and (c) the presence of one or more amino acid sequences selected from the group consisting of YGASPLHXAK, MKDEVFR, EFGEHITK, VMLTGTLSDR, XXGAAPTYFRP and TVFGAK, wherein X represents any amino acid residue.

Certain embodiments provide compositions comprising a purified mammalian calcium independent phospholipase $A_2$/B enzyme.

In other embodiments, the enzyme is further characterized by activity in a mixed micelle assay with 1-palmitoyl-2-[$^{14}$C]-arachidonyl-phosphatidylcholine (preferably a specific activity of about 1 µmol to about 20 µmol per minute per milligram, more preferably a specific activity of about 1 µmol to about 5 µmol per minute per milligram); by a pH optimum of 6; and/or by the absence of stimulation by adenosine triphosphate in the liposome assay.

In other embodiments, the invention provides isolated polynucleotides comprising a nucleotide sequence selected from the group consisting of: (a) the nucleotide sequence of SEQ ID NO:1; (b) a nucleotide sequence encoding the amino acid sequence of SEQ ID NO:2; (c) a nucleotide sequence encoding a fragment of the amino acid sequence of SEQ ID NO:2 having activity in a mixed micelle assay with 1-palmitoyl-2-[$^{14}$C]-arachidonyl-phosphatidylcholine; (d) a nucleotide sequence capable of hybridizing with the sequence of (a), (b) or (c) which encodes a peptide having activity in a mixed micelle assay with 1-palmitoyl-2-[$^{14}$C]-arachidonyl-phosphatidylcholine; and (e) allelic variants of the sequence of (a). Other embodiments provide an isolated polynucleotide comprising a nucleotide sequence selected from the group consisting of: (a) the nucleotide sequence of SEQ ID NO:16; (b) a nucleotide sequence encoding the amino acid sequence of SEQ ID NO:17; (c) a nucleotide sequence encoding a fragment of the amino acid sequence of SEQ ID NO:17 having activity in a mixed micelle assay with 1-palmitoyl-2-[$^{14}$C]-arachidonyl-phosphatidylcholine; (d) the nucleotide sequence of SEQ ID NO:18; (e) a nucleotide sequence encoding the amino acid sequence of SEQ ID NO:19; (f) a nucleotide sequence encoding a fragment of the amino acid sequence of SEQ ID NO:19 having activity in a mixed micelle assay with 1-palmitoyl-2-[$^{14}$C]-arachidonyl-phosphatidylcholine; (g) the nucleotide sequence of SEQ ID NO:20; (h) a nucleotide sequence encoding the amino acid sequence of SEQ ID NO:21; (i) a nucleotide sequence encoding a fragment of the amino acid sequence of SEQ ID NO:21 having activity in a mixed micelle assay with 1-palmitoyl-2-[$^{14}$C]-arachidonyl-phosphatidylcholine; (j) the nucleotide sequence of SEQ ID NO:22; (k) a nucleotide sequence encoding the amino acid sequence of SEQ ID NO:23; (l) a nucleotide sequence encoding a fragment of the amino acid sequence of SEQ ID NO:23 having activity in a mixed micelle assay with 1-palmitoyl-2-[$^{14}$C]-arachidonyl-phosphatidylcholine; (m) a nucleotide sequence capable of hybridizing with the sequence of any of (a)–(l) which encodes a peptide having activity in a mixed micelle assay with 1-palmitoyl-2-[$^{14}$C]-arachidonyl-phosphatidylcholine; and (n) allelic variants of the sequence of (a), (d), (g) or (j). Expression vectors comprising such polynucleotides and host cells transformed with such vectors are also provided by the present invention. Compositions comprising peptides encoded by such polynucleotides are also provided.

The present invention also provides processes for producing a phospholipase enzyme, said process comprising: (a) establishing a culture of the host cell transformed with a $cPLA_2$/B encoding polynucleotide in a suitable culture medium; and (b) isolating said enzyme from said culture. Compositions comprising a peptide made according to such processes are also provided.

Certain embodiments of the present invention provide compositions comprising a peptide comprising an amino acid sequence selected from the group consisting of: (a) the amino acid sequence of SEQ ID NO:2; and (b) a fragment of the amino acid sequence of SEQ ID NO:2 having activity in a mixed micelle assay with 1-palmitoyl-2-[$^{14}$C]-arachidonyl-phosphatidylcholine.

Other embodiments provide compositions comprising a peptide comprising an amino acid sequence selected from the group consisting of: (a) the amino acid sequence of SEQ ID NO:17; (b) a fragment of the amino acid sequence of SEQ ID NO:17 having activity in a mixed micelle assay with 1-palmitoyl-2-[$^{14}$]-arachidonyl-phosphatidylcholine; (c) the amino acid sequence of SEQ ID NO:19; (d) a fragment of the amino acid sequence of SEQ ID NO:19 having activity in a mixed micelle assay with 1-palmitoyl-2-[$^{14}$C]-arachidonyl-phosphatidylcholine; (e) the amino acid sequence of SEQ ID NO:21; (f) a fragment of the amino acid sequence of SEQ ID NO:21 having activity in a mixed micelle assay with 1-palmitoyl-2-[$^{14}$C]-arachidonyl-phosphatidylcholine; (g) the amino acid sequence of SEQ ID NO:23; and (h) a fragment of the amino acid sequence of SEQ ID NO:23 having activity in a mixed micelle assay with 1-palmitoyl-2-[$^{14}$C]-arachidonyl-phosphatidylcholine.

The present invention also provides methods for identifying an inhibitor of phospholipase activity, said method comprising: (a) combining a phospholipid, a candidate inhibitor compound, and a composition comprising a phospholipase enzyme peptide; and (b) observing whether said phospholipase enzyme peptide cleaves said phospholipid and releases fatty acid thereby, wherein the peptide composition is one of those described above. Inhibitor of phospholipase activity identified by such methods, pharmaceutical compositions comprising a therapeutically effective amount of such inhibitors and a pharmaceutically acceptable carrier, and methods of reducing inflammation by administering such pharmaceutical compositions to a mammalian subject are also provided.

Polyclonal and monoclonal antibodies to the peptides of the invention are also provided.

DETAILED DESCRIPTION OF THE INVENTION

Figure 1:
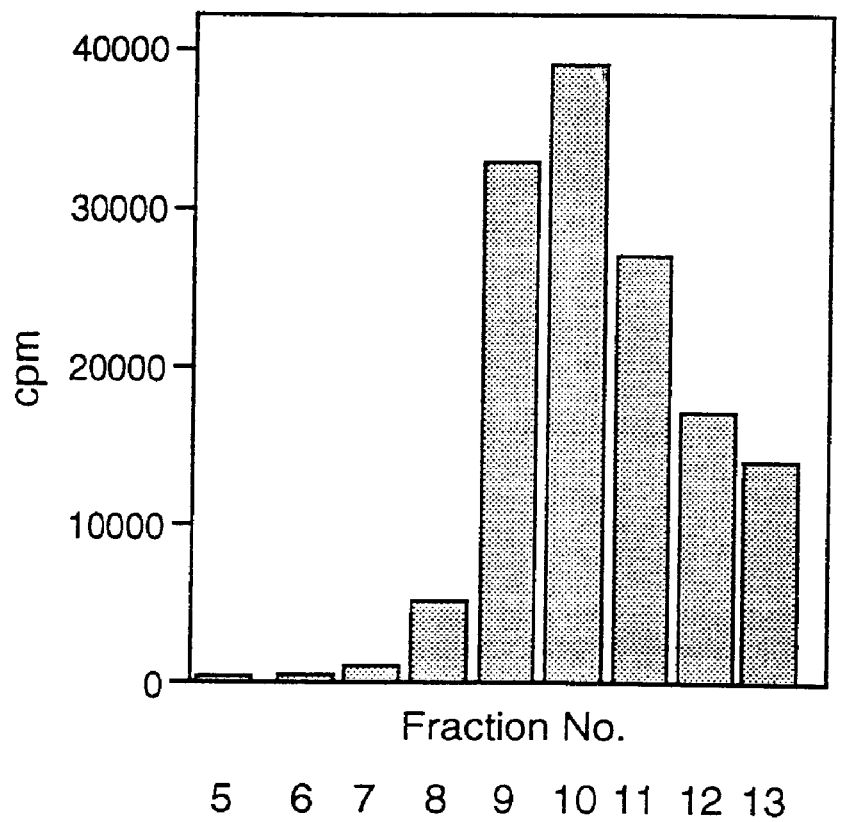
FIG. 1: Fractions containing activity eluted from a Mono P column were examined by reducing SDS-PAGE on a 4–20% gradient gel. Activity of each fraction is show above the gel and the 86 kD band is indicated on the silver stained gel. Molecular weight markers are indicated.
Figure 1:
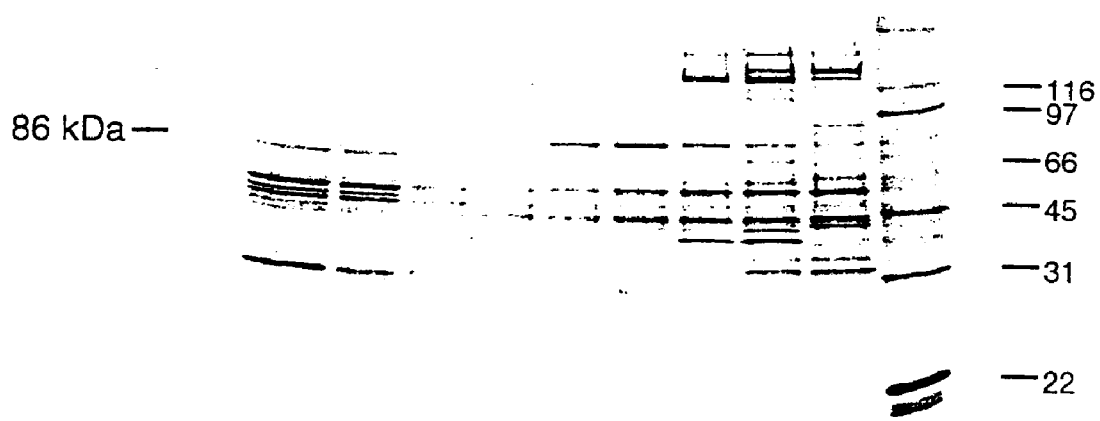
Figure 2:
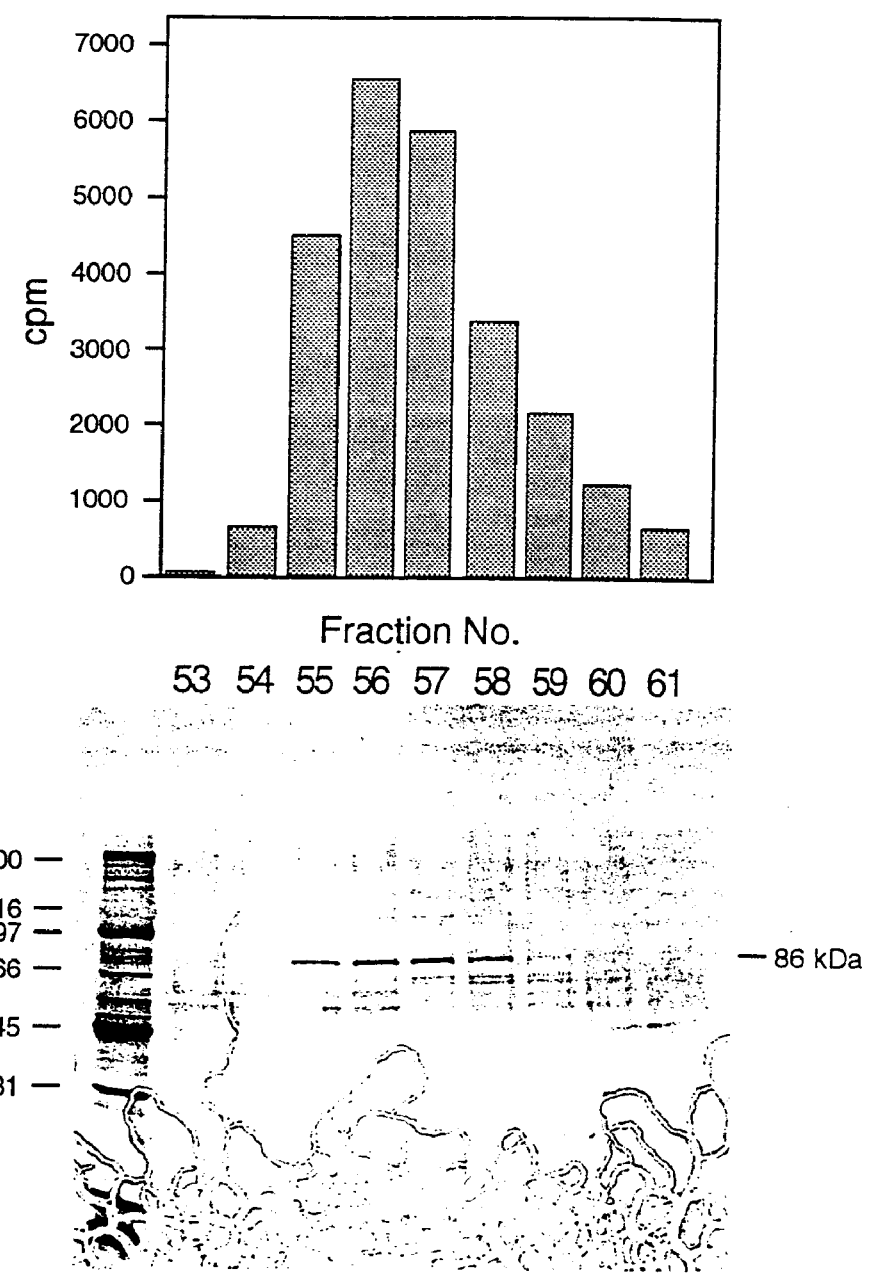
FIG. 2: Active fractions from a Mono p/Heparin column were combined and further purified on a size exclusion column. Activity eluted in the 250–350 kD size range. Examination of the fractions by SDS-PAGE under reducing conditions on 4–20% gel indicated only one protein band correlated with activity at 86 kD. Molecular weight markers are indicated.
Figure 3:
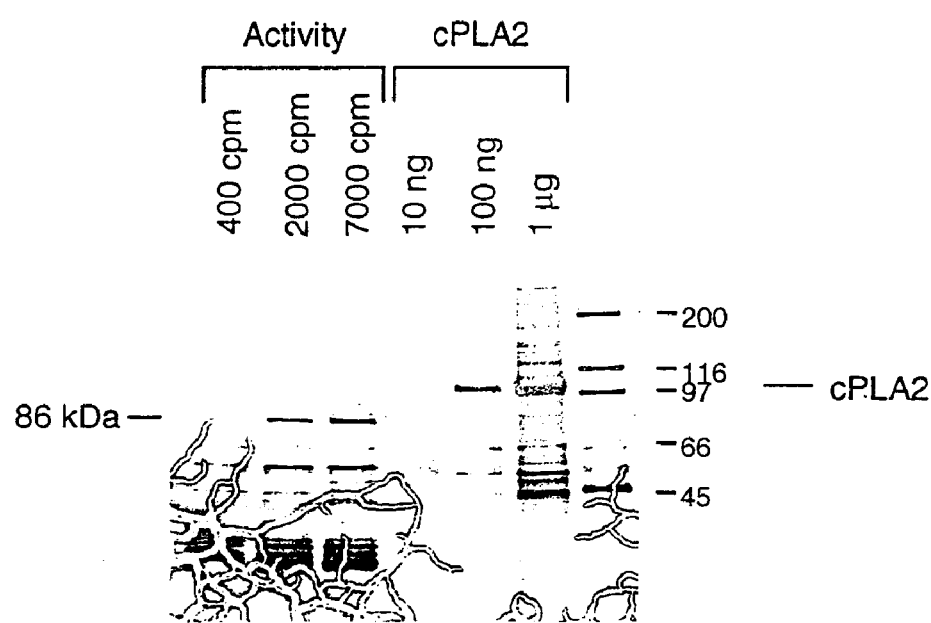
FIG. 3: Active fractions from Mono P eluate and cPLA$_2$ (0.1–1.0 µg) were analyzed on two 4–20% SDS gels under reducing conditions run in parallel. One gel was silver stained (1) and in the other gel the proteins were transferred to nitrocellulose. The blot was then probed with an anti-cPLA$_2$ polyclonal antibody and reactive proteins were visualized with the ECL system (Amersham) (2). Molecular weight markers are indicated.
Figure 3:
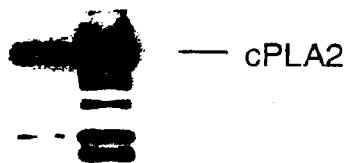
Figure 4:
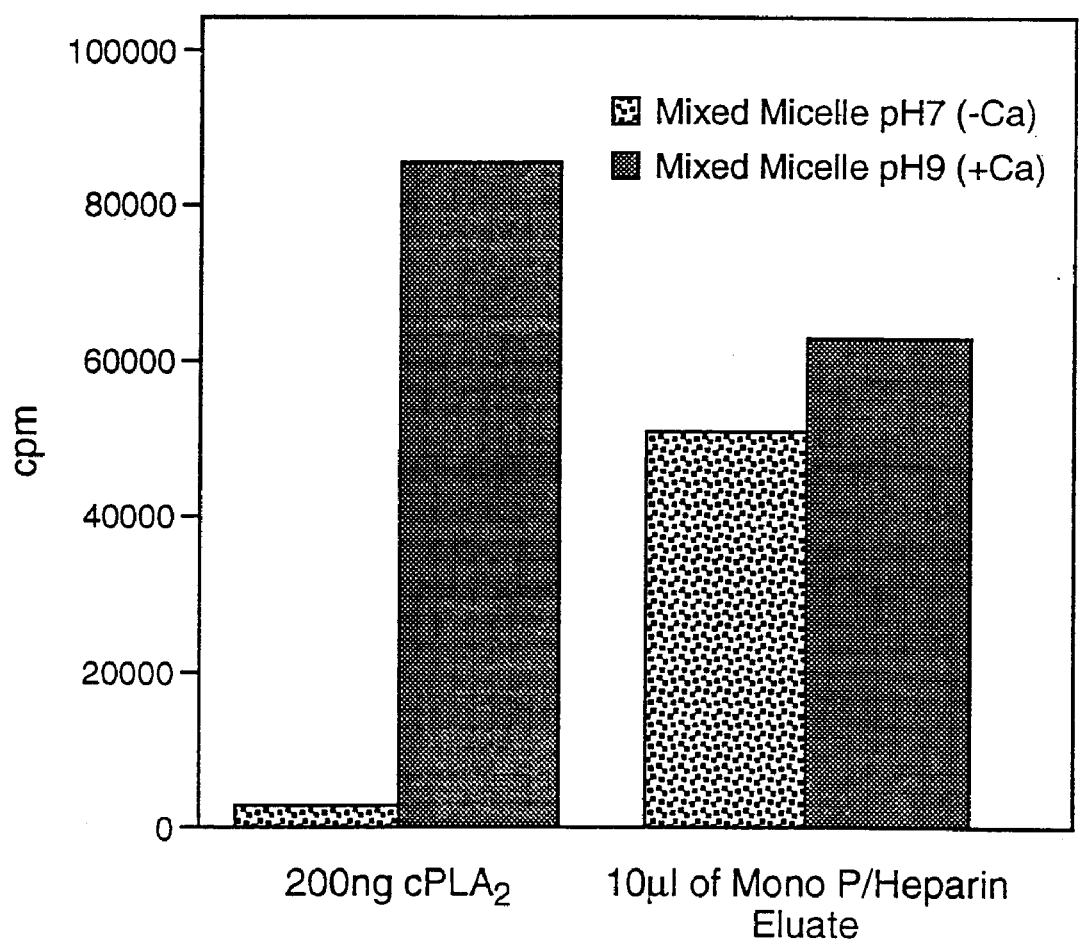
FIG. 4: The activity of the calcium-independent phospholipase eluted from a Mono P/Heparin column and cPLA$_2$ were compared under conditions which favor each enzyme; pH 7, 10% glycerol in the absence of calcium and pH 9, 70% glycerol in the presence of calcium, respectively.
Figure 5:
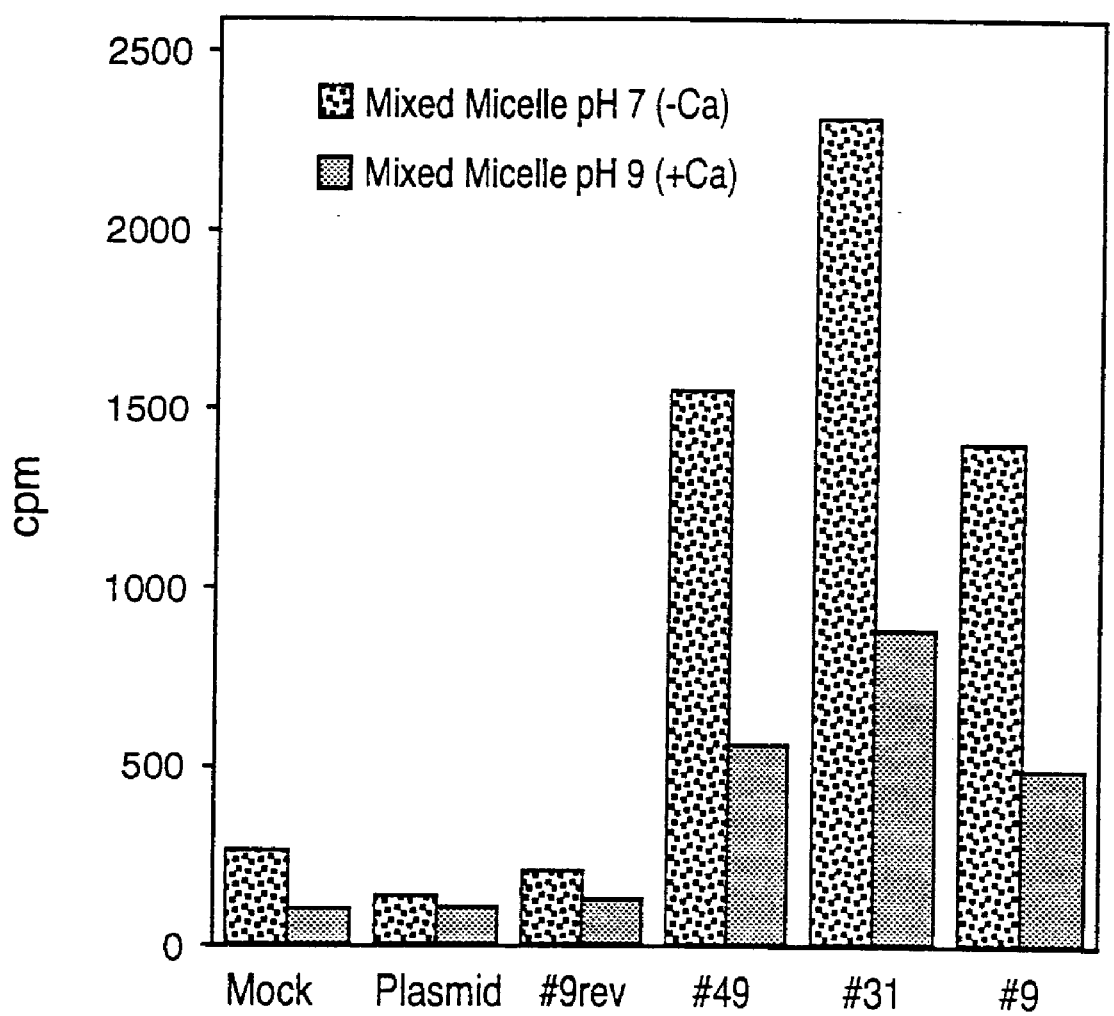
FIG. 5: Activity in the cytosolic extracts of COS cells transfected with: no DNA; plasmid (pED) containing no inserted gene; clone 9 in the antisense orientation; and clones 49, 31 and 9 expressed in pED. The extracts were analyzed under two different assay conditions described for the data presented in FIG. 4.
Figure 6:
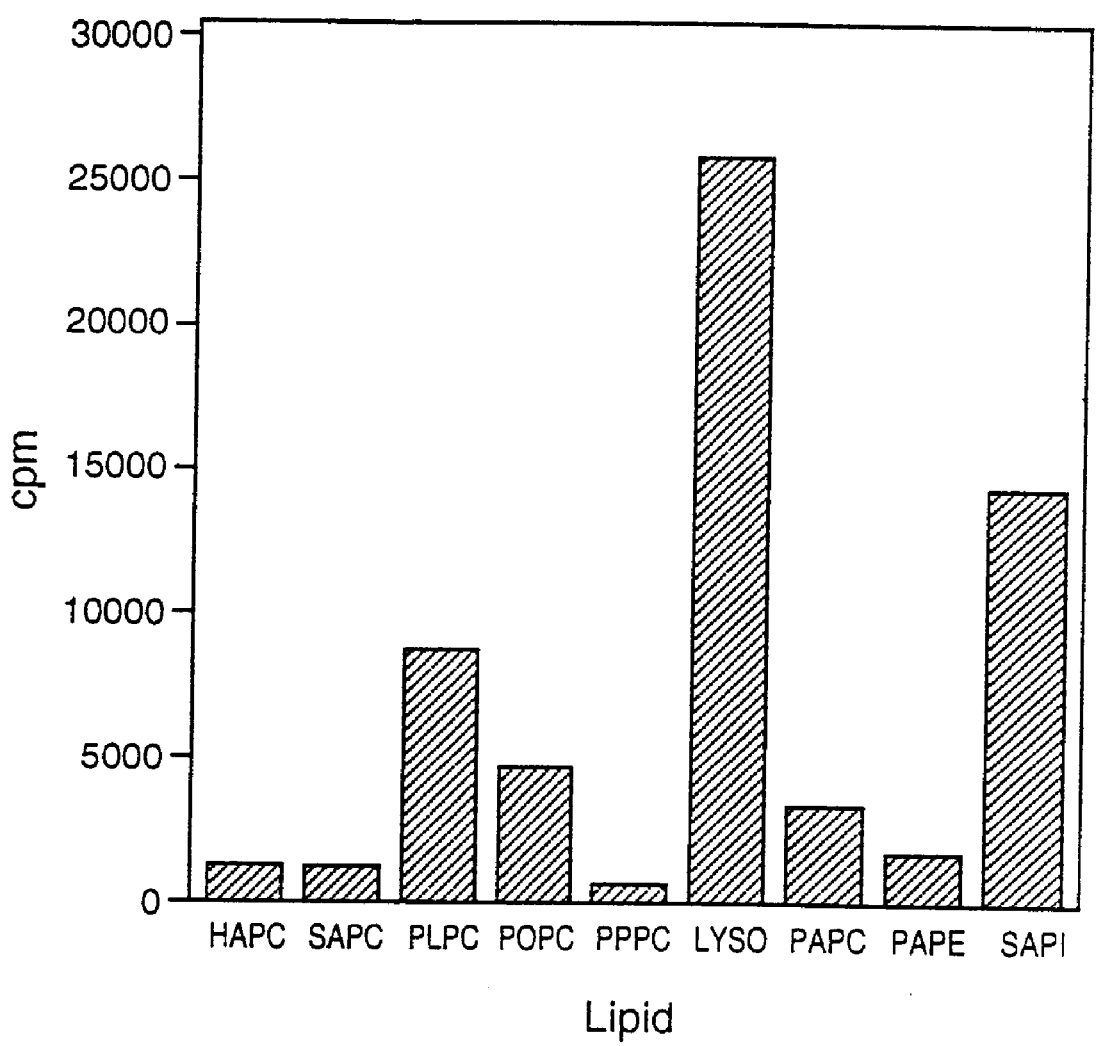
FIG. 6: A comparison of sn-2 fatty acid hydrolysis by activity eluted from a Mono P/Heparin column as a function of the fatty acid substituent at either the sn-1 or sn-2 position and the head group. HAPC, SAPC, PLPC, POPC, PPPC, LYSO and PAPC indicate 1-hexadecyl-2-arachidonyl-, 1-stearoyl-2-arachidonyl-, 1-palmitoyl-2-linoleyl-, 1-palmitoyl-2-oleyl-, 1-palmitoyl-2-palmitoyl-, 1-palmitoyl-, 1-palmitoyl-2-arachidonyl-phosphatidylcholine, respectively. PAPE and SAPI indicate 1-palmitoyl-2-arachidonyl-phosphotidylethanolamine and 1-stearoyl-2-arachidonyl-phosphoinositol, respectively. In all cases the $^{14}$C-labelled fatty acid is in the sn-2 position.

The present inventors have found surprisingly a calcium independent cytosolic phospholipase enzyme, designated calcium independent cytosolic phospholipase A$_2$/B or calcium independent cPLA$_2$/B, purified from the cytosol of Chinese hamster ovary (CHO) cells. The activity was also present in the cytosol of tissues and cell extracts listed in Table I.

TABLE I

| tissue/cell | mixed micelle pH 7 (pmol/min/mg) | liposome pH 7 (pmol/min/mg) |
| --- | --- | --- |
| rat brain | | 1–2 |
| rat heart | | 0.3–0.5 |
| bovine brain | | 0.4 |
| pig heart | 0.8 | |
| CHO-Dukx | 10–20 | 2–5 |
| U937 (ATCC CRL1593) | 2 | |
| FBHE (ATCC CRL1395) | 2 | |
| H9c2 (ATCC Ccl 108) | 15 | |

The enzyme was originally purified by more than 8,000-fold from CHO cells by sequential chromatography on diethylaminoethane (DEAE), phenyl and heparin-toyopearl, followed by chromatofocussing on Mono P (as described further in Example 1). In addition the activity could be further purified by size exclusion chromatography after the Mono P column. The enzyme eluted from the size exclusion chromatography column in the 250–350 kD range, indicating the active enzyme may consist of a multimeric complex, or may possibly be associated with phospholipids.

The calcium independent phospholipase activity correlated with a single major protein band of 86 kD on denaturing sodium dodecyl sulfate polyacrylamide gel electrophoresis (SDS-PAGE) of active fractions from the Mono P and size exclusion chromatographic steps; in the latter no protein bands were observed in the 250–350 kD range. The specific activity of the enzyme is about 1 µmol to about 20 µmol per minute per milligram based on the abundance of the 86 kD band in the most active fractions eluted from the Mono P and size exclusion columns in the mixed micelle assay (Example 3B). The protein band was not recognized by a polyclonal antibody directed against the calcium dependent cPLA$_2$ of U.S. Pat. No. 5,322,776.

The calcium independent phospholipase of the present invention has a pH optimum of 6; its activity is suppressed by calcium (in all assays) and by triton X-100 (in the assay of Example 3A); and is not stimulated by adenosine triphosphate (ATP) (in the assay of Example 3A). The enzyme is inactivated by high concentration denaturants, e.g. urea above 3M, and by detergents, e.g. CHAPS and octyl glucoside. The calcium-independent phospholipase favors hydrolysis by several fold of unsaturated fatty acids, e.g. linoleyl, oleyl and arachidonyl, at the sn-2 position of a phospholipid compared with palmitoyl. In addition there is a preference for palmitoyl at the sn-1 position over hexadecyl or stearoyl for arachidonyl hydrolysis at the sn-2 position. In terms of head group substituents there is a clear preference for inositol over choline or ethanolamine when arachidonyl is being hydrolyzed at the sn-2 position. Further, as with cPLA$_2$ of U.S. Pat. No. 5,322,776, there is a significant lysophospholipase activity, i.e. hydrolysis of palmitoyl at the sn-1 position when there is no fatty acid substituent at the sn-2 position. Finally, hydrolysis of fatty acid substituents in the sn-1 or sn-2 in PAPC were compared where either palmitoyl or arachidonyl were labelled with $^{14}$C. Fatty acids were removed at both positions with the sn-2 position having a higher initial rate of hydrolysis by 2–3 fold. This result may indicate sequential hydrolysis of the arachidonyl substituent followed by rapid cleavage of palmitoyl in the lysophospholipid species, which is suggested by the hydrolysis of the individual lipid species. The similar rates of hydrolysis of fatty acid substituents at the sn-1 (palmitoyl) or sn-2 (arachidonyl) positions, where the radioactive label is in either position, is indicative of a phospholipase B activity. However, the fatty acid substituent at the sn-2 position clearly influences the PLB activity, not the sn-1 fatty acid, since hydrolysis of 1,2-dipalmitoyl substituted phospholipids is substantially less than for the 1-palmitoyl-2-arachidonyl species. These results can be clarified by studying the hydrolysis rates at each position of isotopically dual labelled phospholipids, e.g. $^3$H and $^{14}$C containing fatty acids at the sn-1 and sn-2 positions, respectively. Therefore, it is prudent to designate the enzyme as a phospholipase $A_2$/B.

A cDNA encoding the calcium independent cPLA$_2$/B of the present invention was isolated as described in Example 4. The sequence of the cDNA is reported as SEQ ID NO:1. The amino acid sequence encoded by such cDNA is SEQ ID NO:2. The invention also encompasses allelic variations of the cDNA sequence as set forth in SEQ ID NO:1, that is, naturally-occurring alternative forms of the cDNA of SEQ ID NO: 1 which also encode phospholipase enzymes of the present invention.

Other cDNAs encoding a calcium independent cPLA$_2$/B of the present invention were isolated from human cDNA sources. Two clones identified as "19a" and "19b" were isolated from a Raij cell DNA library derived from Burkitt's lymphoma (ATCC CCL86, commercially available from Clonetech) using a probe derived from the CHO sequence (a 2.1 kb SalI-SmaI fragment). Clones 19a and 19b were deposited with the American Type Culture Collection on Nov. 7, 1995 as accession numbers ATCC 69948 and ATCC 69949. The nucleotide sequences of clones 19a and 19b are reported in SEQ ID NO:16 and SEQ ID NO:18, respectively. SEQ ID NO:17 and SEQ ID:19 report the corresponding amino acid sequences encoded by the coding regions of clones 19a and 19b, respectively. Clones 19a and 19b are both partial clones of the full-length human enzyme.

SEQ ID NO:20 and SEQ ID NO:22 report the nucleotide sequences of alternative ways in which clones 19a and 19b can be spliced to encode a longer partial clone for the full-length human enzyme. The splice occurs after nucleotide 1225 in SEQ ID NO:20 and after nucleotide 1228 in SEQ ID NO:22. The corresponding spliced amino acid sequences are reported in SEQ ID NO:21 and SEQ ID NO:23. Spliced cDNA clones can be made from clones 19a and 19b in accordance with methods known to those skilled in the art.

Full-length clones encoding the human enzyme can be isolated by probing human cDNA libraries containing full-length clones using probes derived from SEQ ID NO:16, SEQ ID NO:18, SEQ ID NO:20 or SEQ ID NO:22.

Also included in the invention are isolated DNAs which hybridize to the DNA sequence set forth in SEQ ID NO:1, SEQ ID NO:16, SEQ ID NO:18, SEQ ID NO:20 or SEQ ID NO:22 under stringent (e.g. 4×SSC at 65° C. or 50% formamide and 4×SSC at 42° C.), or relaxed (4×SSC at 50° C. or 30–40% formamide at 42° C.) conditions.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the phospholipase enzyme peptides recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the phospholipase enzyme peptide is expressed by a host cell which has been transformed (transfected) with the ligated polynucleotide/expression control sequence.

A number of types of cells may act as suitable host cells for expression of the phospholipase enzyme peptide. Suitable host cells are capable of attaching carbohydrate side chains characteristic of functional phospholipase enzyme peptide. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The phospholipase enzyme peptide may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the Max-Bac® kit), and such methods are well known in the art, as described in Summers and Smith, *Texas Agricultural Experiment Station Bulletin No.* 1555 (1987), incorporated herein by reference.

Alternatively, it may be possible to produce the phospholipase enzyme peptide in lower eukaryotes such as yeast or in prokaryotes such as bacteria. Potentially suitable yeast stains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the phospholipase enzyme peptide is made in yeast or bacteria, it is necessary to attach the appropriate carbohydrates to the appropriate sites on the protein moiety covalently, in order to obtain the glycosylated phospholipase enzyme peptide. Such covalent attachments may be accomplished using known chemical or enzymatic methods.

The phospholipase enzyme peptide of the invention may also be expressed as a product of transgenic animals, e.g., as a component of the milk of transgenic cows, goats, pigs, or sheep which are characterized by somatic or germ cells containing a polynucleotide encoding the phospholipase enzyme peptide.

The phospholipase enzyme peptide of the invention may be prepared by culturing transformed host cells under culture conditions necessary to express a phospholipase enzyme peptide of the present invention. The resulting expressed protein may then be purified from culture medium or cell extracts as described in the examples below.

Alternatively, the phospholipase enzyme peptide of the invention is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the phospholipase enzyme peptide from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the phospholipase enzyme peptide. Some or all of the foregoing purification steps, in various combinations, can also be employed to provide a substantially homogeneous isolated recombinant protein. The phospholipase enzyme peptide thus purified is substantially free of other mammalian proteins and is defined in accordance with the present invention as "isolated phospholipase enzyme peptide".

The calcium independent $cPLA_2/B$ of the present invention is distinct from the $cPLA_2$ of U.S. Pat. No. 5,322,776 and from previously-described calcium independent phospholipase $A_2$ enzymes (such as those described by Gross et al., supra; and Ackermann et al., supra). The enzyme of the present invention differs from the $cPLA_2$ of the '776 patent in the following ways:

(1) its activity is not calcium dependent;
(2) it is more active in 10% glycerol than in 70% glycerol;
(3) it has a molecular weight of 86 kD, not 110 kD as for $cPLA_2$;
(4) it has a pH optimum of 6, not greater than 8 as for $cPLA_2$;
(5) it hydrolyzes fatty acids at sn-1 as well as sn-2;
(6) it binds to heparin, while $cPLA_2$ does not;
(7) it elutes from an anion exchange column at 0.1–0.2 M NaCl, while $cPLA_2$ elutes at 0.3–0.4 M NaCl; and
(8) it does not bind to anti-$cPLA_2$ polyclonal antibody.

The enzyme of the present invention differs from the calcium independent enzyme of Gross et al. in the following characteristics:

(1) it has a molecular weight of 86 kD, not 40 kD as for the Gross enzyme;
(2) it is not homologous at the protein level to rabbit skeletal muscle phosphofructokinase in contrast to the 85 kD putative regulatory protein associated with the 40 kD Gross enzyme;
(3) hydrolysis at the sn-2 position is favored by an acyl-linked fatty acid at the sn-1 position in contrast to ether-linked fatty acids with the Gross enzyme;
(4) its does not bind to an ATP column and was not activated by ATP in a liposome assay compared to the Gross enzyme; and
(5) it was active in a mixed micelle assay containing Triton X-100.

The enzyme of the present invention differs from the calcium independent enzyme of Ackermann et al. (the "Dennis enzyme")in the following characteristics:

(1) it does not bind to an ATP column;
(2) it binds to an anion exchange column (mono Q), while the Dennis enzyme remains in the unbound fraction;
(3) it has a molecular weight of 86 kD, not 74 kD as for the Dennis enzyme;
(4) it has substantial lysophospholipase activity and is relatively inactive on phospholipids containing ether-linked fatty acids at the sn-1 position in a liposome assay; and
(5) it appears to hydrolyze fatty acid substituents at the sn-1 and sn-2 positions of a phospholipid, whereas the Dennis enzyme favors hydrolysis at the sn-2 position.

The calcium independent $cPLA_2/B$ of the present invention may be used to screen unknown compounds having anti-inflammatory activity mediated by the various components of the arachidonic acid cascade. Many assays for phospholipase activity are known and may be used with the calcium independent phospholipase $A_2/B$ on the present invention to screen unknown compounds. For example, such an assay may be a mixed micelle assay as described in Example 3. Other known phospholipase activity assays include, without limitation, those disclosed in U.S. Pat. No. 5,322,776. These assays may be performed manually or may be automated or robotized for faster screening. Methods of automation and robotization are known to those skilled in the art.

In one possible screening assay, a first mixture is formed by combining a phospholipase enzyme peptide of the present invention with a phospholipid cleavable by such peptide, and the amount of hydrolysis in the first mixture ($B_0$) is measured. A second mixture is also formed by combining the peptide, the phospholipid and the compound or agent to be screened, and the amount of hydrolysis in the second mixture (B) is measured. The amounts of hydrolysis in the first and second mixtures are compared, for example, by performing a $B/B_0$ calculation. A compound or agent is considered to be capable of inhibiting phospholipase activity (i.e., providing anti-inflammatory activity) if a decrease in hydrolysis in the second mixture as compared to the first mixture is observed. The formulation and optimization of mixtures is within the level of skill in the art, such mixtures may also contain buffers and salts necessary to enhance or to optimize the assay, and additional control assays may be included in the screening assay of the invention.

Other uses for the calcium independent $cPLA_2/B$ of the present invention are in the development of monoclonal and polyclonal antibodies. Such antibodies may be generated by employing purified forms of the calcium independent $cPLA_2$ or immunogenic fragments thereof as an antigen using standard methods for the development of polyclonal and monoclonal antibodies as are known to those skilled in the art. Such polyclonal or monoclonal antibodies are useful as research or diagnostic tools, and further may be used to study phospholipase $A_2$ activity and inflammatory conditions.

Pharmaceutical compositions containing anti-inflammatory agents (i.e., inhibitors) identified by the screening method of the present invention may be employed to treat, for example, a number of inflammatory conditions such as rheumatoid arthritis, psoriasis, asthma, inflammatory bowel disease and other diseases mediated by increased levels of prostaglandins, leukotriene, or platelet activating factor. Pharmaceutical compositions of the invention comprise a therapeutically effective amount of a calcium independent cPLA$_2$ inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 μg to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

Administration is preferably intravenous, but other known methods of administration for anti-inflammatory agents may be used. Administration of the anti-inflammatory compounds identified by the method of the invention can be carried out in a variety of conventional ways. For example, for topical administration, the anti-inflammatory compound of the invention will be in the form of a pyrogen-free, dermatologically acceptable liquid or semi-solid formulation such as an ointment, cream, lotion, foam or gel. The preparation of such topically applied formulations is within the skill in the art. Gel formulation should contain, in addition to the anti-inflammatory compound, about 2 to about 5% W/W of a gelling agent. The gelling agent may also function to stabilize the active ingredient and preferably should be water soluble. The formulation should also contain about 2% W/V of a bactericidal agent and a buffering agent. Exemplary gels include ethyl, methyl, and propyl celluloses. Preferred gels include carboxypolymethylene such as Carbopol (934P; B. F. Goodrich), hydroxypropyl methylcellulose phthalates such as Methocel (K100M premium; Merril Dow), cellulose gums such as Blanose (7HF; Aqualon, U.K.), xanthan gums such as Keltrol (TF; Kelko International), hydroxyethyl cellulose oxides such as Polyox (WSR 303; Union Carbide), propylene glycols, polyethylene glycols and mixtures thereof. If Carbopol is used, a neutralizing agent, such as NaOH, is also required in order to maintain pH in the desired range of about 7 to about 8 and most desirably at about 7.5. Exemplary preferred bactericidal agents include steryl alcohols, especially benzyl alcohol. The buffering agent can be any of those already known in the art as useful in preparing medicinal formulations, for example 20 mM phosphate buffer, pH 7.5.

Cutaneous or subcutaneous injection may also be employed and in that case the anti-inflammatory compound of the invention will be in the form of pyrogen-free, parenterally acceptable aqueous solutions. The preparation of such parenterally acceptable solutions, having due regard to pH, isotonicity, stability, and the like, is within the skill in the art.

Intravenous injection may be employed, wherein the anti-inflammatory compound of the invention will be in the form of pyrogen-free, parenterally acceptable aqueous solutions. A preferred pharmaceutical composition for intravenous injection should contain, in addition to the anti-inflammatory compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition according to the present invention may also contain stabilizers, preservatives, buffers, antioxidants, or other additive known to those of skill in the art.

The amount of anti-inflammatory compound in the pharmaceutical composition of the present invention will depend upon the nature and severity of the condition being treated, and on the nature of prior treatments which the patient has undergone. Ultimately, the attending physician will decide the amount of anti-inflammatory compound with which to treat each individual patient.

Anti-inflammatory compounds identified using the method of the present invention may be administered alone or in combination with other anti-inflammation agents and therapies.

EXAMPLE 1

Purification of Calcium Independent cPLA$_2$

A) Preparation of CHO-Dukx Cytosolic Fraction:

CHO cells, approximately $5\times10^{11}$ cells from a 250L culture, were concentrated by centrifugation and rinsed once with phosphate-buffered saline and reconcentrated. The cell slurry was frozen in liquid nitrogen and stored at −80° C. at $4\times10^{11}$ cells/kg of pellet. The CHO pellets were processed in 0.5 kg batches by thawing the cells in 1.2L of 20 mM imidazol pH 7.5, 0.25M sucrose, 2 mM EDTA, 2 mM EGTA, 1 μg/ml leupeptin, 5 μg/ml aprotinin, 5 mM DTT and 1 mM PMSF ("Extraction Buffer"). The cells were transferred to a Parr bomb at 4° C. and pressurized at 600 psi for 5 minutes and lysed by releasing the pressure. The supernatant was centrifuged at 10,000×g for 30 minutes and subsequently at 100,000×g for 60 minutes.

B) DEAE Anion Exchange Chromatography:

The cytosolic fraction (10 gm protein) was diluted to 5 mg/ml with 20 mM imidazol pH 7.5, 5 mM DTT, 1 mM EDTA and 1 mM EGTA (Buffer A) and applied to a 1L column of DEAE toyopearl equilibrated in buffer A at 16 ml/min. The column was washed to background absorbance ($A_{280}$) with buffer A and developed with a gradient of 0–0.5M NaCl in buffer A over 240 minutes with one minute fractions. The first activity peak at 100–150 mM NaCl was collected.

C) Hydrophobic Interaction and Heparin Toyopearl Chromatography:

The DEAE fractions (4 gm of protein at 3 mg/ml) were made 0.5M in ammonium sulfate and applied at 10 ml/min to a 300 ml phenyl toyopearl column equilibrated in buffer A containing 0.5M ammonium sulfate. The column was washed to background absorbance ($A_{280}$). The column was then developed with a gradient of 0.5–0.2M (15 minutes) then 0.2–0.0 M ammonium sulfate (85 minutes). The column was then connected in tandem to a 10 ml heparin column equilibrated in buffer A and elution was continued for 18 hours at 1.5 ml/min with buffer A. The phenyl column was disconnected and the activity was eluted from the heparin column by applying 0.5M NaCl in buffer A at 2 ml/min.

D) Chromatofocussing Chromatography:

A portion of the above active fractions (16 mg) was dialyzed exhaustively against 20 mM Bis-Tris pH 7, 10% glycerol, 1M urea and 5 mM DTT and applied at 0.5 ml/min to a Mono P 5/20 column equilibrated with the same buffer. The column was washed with the same buffer to background absorbance ($A_{280}$) and a pH gradient was established by applying 10% polybuffer 74 pH 5, 10% glycerol, 1M urea and 5 mM DTT.

The relative purification of the enzyme of the present invention at each step of the foregoing purification scheme is summarized in Table II.

TABLE II

| Step | Protein (mg) | Activity (u**) | Specific Activity (u/mg) | Fold Purification | Yield (%) |
|---|---|---|---|---|---|
| cytosolic extract* | 126,000 | 2050 | 0.016 | — | — |
| DEAE | 16,000 | 1264 | 0.079 | 5 | 60 |
| phenyl/ heparin | 193 | 90 | 0.46 | 30 | 4.5 |
| Mono P | 0.1–0.2 | 14 | 140 | 8,000 | 0.7 |

*Extract from 3.5 kg of frozen CHO cell pellet
**1 unit is defined as the amount of activity that releases 1 nmol of arachidonic acid per minute The phospholipase can be further purified by the following steps:

E) Heparin Chromatography:

The sample from (D) above is applied at 0.5 ml/min onto a heparin column (maximum capacity 10 mg protein/ml of resin), equilibrated in buffer A. The activity is eluted by 0.4M NaCl in buffer A.

F) Size Exclusion Chromatography:

The active fractions from the heparin column are applied to two TSK G3000SW$_{XL}$ columns (7.8 mm×30 cm) linked in tandem equilibrated with 150 mM NaCl in buffer A at 0.3 ml/min. Phospholipase activity elutes in the 250–350 kD size range.

Recombinant enzyme may also be purified in accordance with this example.

EXAMPLE 2

Amino Acid Sequencing

A portion (63 µg total protein) of the Mono P active fractions was concentrated on a heparin column, as described above. The sample, 0.36 ml was mixed with an equal volume of buffer A and 10% SDS, 10 µl and concentrated to 40 µl on an Amicon-30 microconcentrator. The sample was diluted with buffer A, 100 µl, concentrated to 60 µl and diluted with Laemmli buffer (2×), 40 µl. The solution was boiled for 5 minutes and loaded in three aliquots on a 4–20% gradient SDS-PAGE mini gel. The sample was electophoresed for two hours at 120 v, stained for 20 minutes in 0.2% Blue R-250, 20% methanol and 0.5% acetic acid and destained in 30% methanol (Rosenfeld et. al. Anal. Biochem. 203, pp. 173–179, 1992). Briefly, the protein bands corresponding to the phospholipase were excised from the gel with a razor blade and washed with 4 150 µl aliquots of 200 mM $NH_4HCO_3$, 50% acetonitrile, for a total of 2 hours. The gel pieces were allowed to air dry for approximately 5 minutes, then partially rehydrated with 1 µl of 200 mM $NH_4HCO_3$, 0.02% Tween 20 (Pierce) and 2 µl of 0.25 µg/µl trypsin (Promega). Gel slices were placed into the bottom of 500 µl mini-Eppendorf tubes, covered with 30 µl 200 mM $NH_4HCO_3$, and incubated at 37° C. for 15 hours. After 1–2 minutes of centrifugation in an Eppendorf microfuge, the supernatants were removed and saved. Peptides in the gel slices were extracted by agitation for a total of 40 minutes with 2 100 µl aliquots of 60% acetonitrile, 0.1% TFA. The extracts were combined with the previous supernatant. The volume was reduced by lyophilization to about 150 µl, and then the sample was diluted with 750 µl 0.1% TFA. Peptide maps were run on an ABI 130A Separation System HPLC and an ABI 30×2.1 mm RP-300 column. The gradient used was as follows: 0–13.5 minutes 0% B, 13.5–63.5 minutes 0–100% B and 63.5–68.5 minutes 100% B, where A is 0.1% TFA and B is 0.085% TFA, 70% acetonitrile. Peptides were then sequenced on an ABI 470A gas-phase sequencer.

EXAMPLE 3

Phopholipase Assays 1. sn-2 Hydrolysis Assays

A) Liposome: The lipid, e.g. 1-palmitoyl-2-[$^{14}$C] arachidonyl-sn-glycero-3-phosphocholine (PAPC), 55 mCi/mmol, was dried under a stream of nitrogen and solubilized in ethanol. The assay buffer contained 100 mM Tris-HCl pH 7, 4 mM EDTA, 4 mM EGTA, 10% glycerol and 25 µM of labelled PAPC, where the volume of ethanol added was no more than 10% of the final assay volume. The reaction was incubated for 30 minutes at 37° C. and quenched by the addition of two volumes of heptane:isopropanol:0.5M sulfuric acid (105:20:1 v/v). Half of the organic was applied to a disposable silica gel column in a vacuum manifold positioned over a scintillation vial, and the free arachidonic was eluted by the addition of ethyl ether (1 ml). The level of radioactivity was measured by liquid scintillation.

Variations on this assay replace EDTA and EGTA with 10 mM $CaCl_2$.

B) Mixed Micelle Basic: The lipid was dried down as in (A) and to this was added the assay buffer consisting of 80 mM glycine pH 9, 5 mM $CaCl_2$ or 5 mM EDTA, 10% or 70% glycerol and 200 µM triton X-100. The mixture was then sonicated for 30–60 seconds at 4° C. to form mixed micelles.

C) Mixed Micelle Neutral: As for (B) except 100 mM Tris-HCl pH 7 was used instead of glycine as the buffer.

2. sn-1 Hydrolysis Assays

Sn-1 hydrolysis assays are performed as described above for sn-1 hydrolysis, but using phospholipids labelled at the sn-1 substituent, e.g. 1-[$^{14}$C]-palmitoyl-2-arachidonyl-sn-glycero-3-phophocholine.

EXAMPLE 4

Cloning of Calcium Independent cPLA$_2$/B

A) cDNA Library Construction

Total RNA was first prepared from 2×10$^8$ CHO-DUX cells using the RNAgents total RNA kit (Promega, Madison, Wis.) and further purified using the PolyATract mRNA Isolation System (Promega) to yield 13.2 µg polyA+ mRNA. Double stranded cDNA was prepared by the Superscript Choice System (Gibco/BRL, Gaithersburg, Md.) starting with 2 µg of CHO-DUX mRNA and using oligo dT primer. The cDNA was modified at both ends by addition of an EcoRI adapter/linker provided by the kit. These fragments were then ligated into the predigested lambda ZAPII/EcoRI vector, and packaged into phage particles with Gigapack Gold packaging extracts (Stratagene, La Jolla, Calif.).

B) Oligonucleotide Probe Design

Several of the peptide sequences determined for the purified calcium independent PLA$_2$/B were selected to design oligonucleotide probes. The amino acid sequence from amino acid 361 to 367 of SEQ ID NO:2 was used to design two degenerate oligonucleotide pools of 17 residues each. Pool 1 is 8-fold degenerate representing the sense strand for amino acids 361 to 366 of SEQ ID NO:2, and pool 2 is 12-fold degenerate representing the antisense strand for amino acids 362–367 of SEQ ID NO:2. Two other degenerate pools were also made from other sequences. Pool 3 is 32-fold degenerate and represents the sense strand for amino acids 490 to 495 of SEQ ID NO:2, and pool 4 is 64-fold degenerate representing the antisense strand for amino acids 513 to 518 of SEQ ID NO:2.

C) Library Screening

Approximately 400,000 recombinant bacteriophage from the CHO-DUX cDNA library were plated and duplicate nitrocellulose filters were prepared. One set of filters was hybridized with pool 1 and the other with pool 2 using tetramethylammonium chloride buffer conditions (Jacobs et al., Nature, 1985, 313, 806). Twelve positive bacteriophages were identified and plated for further analysis. Three sets of nitrocellulose filters were prepared from this plating and hybridized with pools 2, 3 and 4, to represent the three peptide sequences from which probes were designed. Several clones were positive for all three pools. Individual bacteriophage plaques were eluted and ampicillin resistant plasmid colonies were prepared following the manufacturer's protocols (Stratagene). Plasmid DNA was prepared for clones 9, 17, 31 and 49, and restriction digests revealed 3.0 kb inserts. Analysis of a portion of the DNA sequence in these clones confirmed that they contained several cPLA$_2$/B peptide sequences and represented the complete coding region of the gene. Clone 9 was selected for complete DNA sequence determination. The sequence of clone 9 is reported as SEQ ID NO:1.

Clone 9 was deposited with ATCC on Jul. 27, 1994 as accession number 69669.

EXAMPLE 5

Expression of Recombinant cPLA$_2$/B

A) Expression in COS Cells

Clone 9 from Example 4 was excised inserted into a SalI site that was engineered into the EcoRI site of the COS expression vector, PMT-2, a beta lactamase derivative of p91023 (Wong et al., Science, 1985, 228, 810). 8 µg of plasmid DNA was then transfected into 1×10$^6$ COS cells in a 10 cm dish by the DEAE dextran protocol (Sompayrac et al., Proc. Natl. Acad. Sci. USA, 1981, 78, 7575) with the addition of a 0.1 mM chloroquine to the transfection medium, followed by incubation for 3 hours at 37° C. The cells were grown in conventional media (DME, 10% fetal calf serum). At 40–48 hours post-transfection the cells were washed twice and then incubated at 37° C. in PBS, 1 mM EDTA (5 ml). The cells were then collected by centrifugation, resuspended in Extraction Buffer (0.5 ml), and lysed by 20 strokes in a Dounce at 4° C. The lysate was clarified by centrifugation and 10–50 µl of the cytosolic fraction was assayed in the neutral and pH 9 mixed micelle assays.

Figure 7:
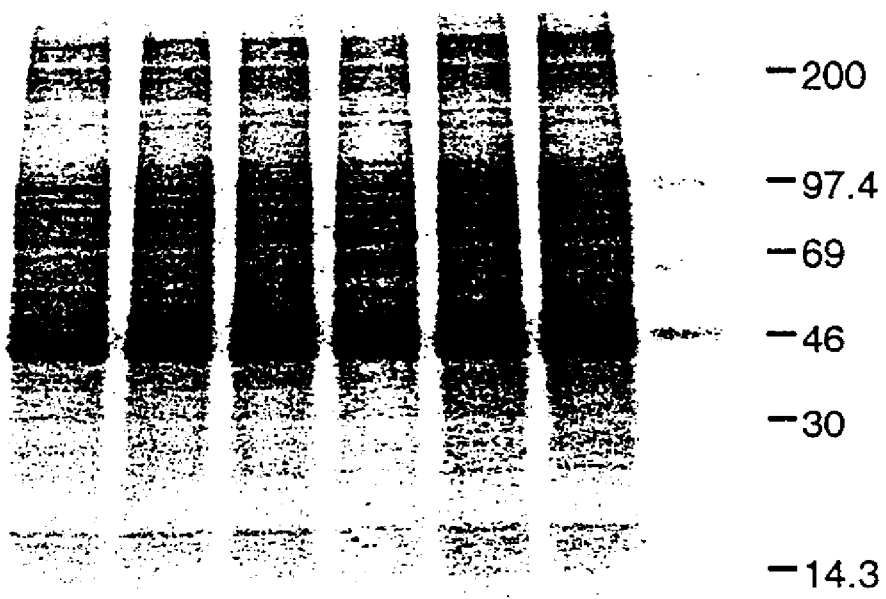
FIG. 7: A 4–20% SDS-PAGE of lysates (5×10$^{10}$ cpm/lane) of $^{35}$S-methionine labelled COS cells transfected with, no DNA, pED (no insert), clone 9 reverse orientation, clones 9, 31 and 49; lanes 1–6, respectively. Molecular weight markers are indicated.

In a further experiment, COS cells were transiently transfected according to established procedures (Kaufman et al.). After 40–48 hours post-transfection the cells wer labelled with $^{35}$S-methionine, 200 µCi per 10 cm plate, for one hour and the cells were lysed in NP-40 lysis buffer (Kaufman et al.). The cell lysates were analyzed by SDS-PAGE on a 4–20% reducing gel where equal counts were loaded per lane. There was an additional protein band at 84–86 kD in the lysates from cells transfected with clones 9, 31 and 49, but not in controls (see FIG. 7).

B) Expression in CHO Cells

A single plasmid bearing both the cPLA$_2$/B encoding sequence and a DHFR gene, or two separate plasmids bearing such sequences, are introduced into DHFR-deficient CHO cells (such as Dukx-BII) by calcium phosphate coprecipitation and transfection. DHFR expressing transformants are selected for growth in alpha media with dialyzed fetal calf serum. Transformants are checked for expression of recombinant enzyme by bioassay, immunoassay or RNA blotting and positive pools are subsequently selected for amplification by growth in increasing concentrations of methotrexate (MTX) (sequential steps in 0.02, 0.2, 1.0 and 5 µM MTX) as described in Kaufman et al., Mol. Cell Biol., 1983, 5, 1750. The amplified lines are cloned and recombinant enzyme expression is monitored by the mixed micelle assay. Recombinant enzyme expression is expected to increase with increasing levels of MTX resistance.

EXAMPLE 6

Mutagenesis of Serine Residues

Ser252 and Ser465 of the murine cPLA$_2$/B amino acid sequence were mutated to alanine residues using the Chamelon Mutagenesis kit (Stratagene) using oligonucleotides CATGGGACCCGCTGGCTTTCC (SEQ ID NO:24) and GGCAGGAACCGCCACTGGGGGC (SEQ ID NO:25), respectively. PLA$_2$ activity was abrogated by changing Ser465 to Ala in the lipase consensus sequence (GXSXGG) surrounding that residue. Although Ser252 is found in a partial lipase motif, mutagenesis did not result in loss of activity. Moreover, Ser465, and the lipase consensus sequence surrounding this residue, are conserved in the human sequence (see amino acids 462–467 of SEQ ID NO:21 and 463–468 of SEQ ID NO:23), while Ser252 is not. On this basis, it is believed that this conserved serine residue is required for activity.

Patent and literature references cited herein are incorporated by reference as if fully set forth.

What is claimed is:

1. A composition comprising a peptide comprising an amino acid sequence selected from the group consisting of:
   (a) the amino acid sequence of SEQ ID NO:17;
   (b) a fragment of the amino acid sequence of SEQ ID NO:17 having activity in a mixed micelle assay with 1-palmitoyl-2-[$^{14}$C]-arachidonyl-phosphatidylcholine;
   (c) the amino acid sequence of SEQ ID NO:19;
   (d) a fragment of the amino acid sequence of SEQ ID NO:19 having activity in a mixed micelle assay with 1-palmitoyl-2-[$^{14}$C]-arachidonyl-phosphatidylcholine;
   (e) the amino acid sequence of SEQ ID NO:21;
   (f) a fragment of the amino acid sequence of SEQ ID NO:21 having activity in a mixed micelle assay with 1-palmitoyl-2-[$^{14}$C]-arachidonyl-phosphatidylcholine;
   (g) the amino acid sequence of SEQ ID NO:23; and
   (h) a fragment of the amino acid sequence of SEQ ID NO:23 having activity in a mixed micelle assay with 1-palmitoyl-2-[$^{14}$C]-arachidonyl-phosphatidylcholine.

2. The composition of claim 1, wherein said peptide comprises the amino acid sequence of SEQ ID NO:17.

3. The composition of claim 1, wherein said peptide comprises the amino acid sequence of SEQ ID NO:19.

4. The composition of claim 1, wherein said peptide comprises the amino acid sequence of SEQ ID NO:21.

5. The composition of claim 1, wherein said peptide comprises the amino acid sequence of SEQ ID NO:23.

6. An isolated polypeptide comprising an amino acid sequence selected from the group consisting of:
   a) the amino acid sequence of SEQ ID NO:17;
   b) a fragment of the amino acid sequence of SEQ ID NO:17 having activity in a mixed micelle assay with 1-palmitoyl-2-[$^{14}$C]-arachidonyl-phosphatidylcholine;
   c) the amino acid sequence of SEQ ID NO:19;
   d) a fragment of the amino acid sequence of SEQ ID NO:19 having activity in a mixed micelle assay with 1-palmitoyl-2-[$^{14}$C]-arachidonyl-phosphatidylcholine;
   e) the amino acid sequence of SEQ ID NO:21;
   f) a fragment of the amino acid sequence of SEQ ID NO:21 having activity in a mixed micelle assay with 1-palmitoyl-2-[$^{14}$C]-arachidonyl-phosphatidylcholine;
   g) the amino acid sequence of SEQ ID NO:23; and
   h) a fragment of the amino acid sequence of SEQ ID NO:23 having activity in a mixed micelle assay with 1-palmitoyl-2-[$^{14}$C]-arachidonyl-phosphatidylcholine.

7. The polypeptide of claim 6, wherein said polypeptide comprises the amino acid sequence of SEQ ID NO:17.

8. The polypeptide of claim 6, wherein said polypeptide comprises the amino acid sequence of SEQ ID NO:19.

9. The polypeptide of claim 6, wherein said polypeptide comprises the amino acid sequence of SEQ ID NO:21.

10. The polypeptide of claim 6, wherein said polypeptide comprises the amino acid sequence of SEQ ID NO:23.

11. An isolated polypeptide encoded by a nucleic acid molecule comprising the nucleotide sequence of SEQ ID NO:16, SEQ ID NO:18, SEQ ID NO:20, SEQ ID NO:22, the DNA insert of the plasmid deposited with ATCC as Accession Number 69948 or 69949, or a complement thereof.

12. An isolated polypeptide comprising the amino acid sequence of SEQ ID NO:17, SEQ ID NO:19, SEQ ID NO:21, SEQ ID NO:23, or an amino acid sequence encoded by the DNA insert of the plasmid deposited with ATCC as Accession Number 69948 or 69949.

13. An isolated naturally-occurring allelic variant of a polypeptide comprising the amino acid sequence of SEQ ID NO: 17, SEQ ID NO: 19, SEQ ID NO: 21, SEQ ID NO: 23, or an amino acid sequence encoded by the DNA insert of the plasmid deposited with ATCC as Accession Number 69948 or 69949, wherein the allelic variant has activity in a mixed micelle assay with 1-palmitoyl-2-[$^{14}$C]-arachidonyl-phosphatidylcholine, and is encoded by a nucleic acid molecule which hybridizes to a compliment of a nucleic acid molecule comprising SEQ ID NO: 16, SEQ ID NO: 18, SEQ ID NO: 20, or SEQ ID NO: 22 under stringent conditions.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 2935 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iii) ANTI-SENSE: NO (ix) FEATURE:
        (A) NAME/KEY: CDS
        (B) LOCATION: 96..2352

(xi) SEQUENCE DESCRIPTION: SEQ ID NO: 1:

```
GCGGCCGCGT CGACGAAGTA AGCGGGCGGA GAAGTGCTGA GTAAGCCGAG AGTAAGGGGG      60

CAGGCTGTCC CCCCCCCCA CCTGCCCCAC GGAGG ATG CAG TTC TTC GGA CGC        113
                                     Met Gln Phe Phe Gly Arg
                                       1               5

CTT GTC AAC ACC CTC AGT AGT GTC ACC AAC TTG TTC TCA AAC CCA TTC      161
Leu Val Asn Thr Leu Ser Ser Val Thr Asn Leu Phe Ser Asn Pro Phe
             10                  15                  20

CGG GTG AAG GAG ATA TCT GTG GCT GAC TAT ACC TCA CAT GAA CGT GTT      209
Arg Val Lys Glu Ile Ser Val Ala Asp Tyr Thr Ser His Glu Arg Val
         25                  30                  35

CGA GAG GAA GGG CAG CTG ATC CTG TTC CAG AAT GCT TCC AAT CGC ACC      257
Arg Glu Glu Gly Gln Leu Ile Leu Phe Gln Asn Ala Ser Asn Arg Thr
     40                  45                  50

TGG GAC TGC ATC CTG GTC AGC CCT AGG AAC CCA CAT AGT GGC TTC CGA      305
Trp Asp Cys Ile Leu Val Ser Pro Arg Asn Pro His Ser Gly Phe Arg
 55                  60                  65                  70

CTC TTC CAG CTG GAG TCA GAG GCA GAT GCC CTG GTG AAC TTC CAG CAG      353
Leu Phe Gln Leu Glu Ser Glu Ala Asp Ala Leu Val Asn Phe Gln Gln
                 75                  80                  85

TTC TCC TCC CAG CTG CCA CCC TTC TAC GAG AGC TCT GTG CAG GTC CTG      401
Phe Ser Ser Gln Leu Pro Pro Phe Tyr Glu Ser Ser Val Gln Val Leu
             90                  95                 100

CAT GTG GAG GTG CTG CAG CAC CTG TCT GAC CTG ATC CGA AGC CAC CCC      449
His Val Glu Val Leu Gln His Leu Ser Asp Leu Ile Arg Ser His Pro
        105                 110                 115

AGC TGG ACG GTG ACA CAC CTG GCG GTG GAG CTT GGC ATT CGG GAG TGC      497
Ser Trp Thr Val Thr His Leu Ala Val Glu Leu Gly Ile Arg Glu Cys
    120                 125                 130

TTC CAC CAC AGC CGC ATC ATC AGC TGC GCC AAC AGC ACA GAG AAT GAG      545
Phe His His Ser Arg Ile Ile Ser Cys Ala Asn Ser Thr Glu Asn Glu
135                 140                 145                 150

GAG GGC TGC ACC CCA CTG CAT TTG GCA TGC CGC AAG GGT GAC AGT GAG      593
Glu Gly Cys Thr Pro Leu His Leu Ala Cys Arg Lys Gly Asp Ser Glu
                155                 160                 165

ATC CTG GTG GAG TTG GTA CAG TAC TGC CAT GCC CAA ATG GAT GTC ACT      641
Ile Leu Val Glu Leu Val Gln Tyr Cys His Ala Gln Met Asp Val Thr
            170                 175                 180

GAC AAC AAA GGA GAG ACG GCC TTC CAT TAC GCT GTA CAA GGG GAC AAT      689
```

```
                 Asp Asn Lys Gly Glu Thr Ala Phe His Tyr Ala Val Gln Gly Asp Asn
                         185                 190                 195

TCC CAG GTG CTG CAG CTC CTA GGA AAG AAC GCC TCA GCT GGC CTG AAC              737
Ser Gln Val Leu Gln Leu Leu Gly Lys Asn Ala Ser Ala Gly Leu Asn
    200                 205                 210

CAG GTG AAC AAA CAA GGG CTA ACT CCA CTG CAC CTG GCC TGC CAG ATG              785
Gln Val Asn Lys Gln Gly Leu Thr Pro Leu His Leu Ala Cys Gln Met
215                 220                 225                 230

GGG AAG CAG GAG ATG GTA CGC GTC CTG CTG CTT TGC AAT GCC CGC TGC              833
Gly Lys Gln Glu Met Val Arg Val Leu Leu Leu Cys Asn Ala Arg Cys
                235                 240                 245

AAC GTC ATG GGA CCC AGT GGC TTT CCC ATC CAC ACA GCC ATG AAG TTC              881
Asn Val Met Gly Pro Ser Gly Phe Pro Ile His Thr Ala Met Lys Phe
                250                 255                 260

TCC CAG AAG GGG TGT GCT GAA ATG ATT ATC AGC ATG GAC AGC AGC CAG              929
Ser Gln Lys Gly Cys Ala Glu Met Ile Ile Ser Met Asp Ser Ser Gln
        265                 270                 275

ATC CAC AGC AAG GAT CCT CGC TAT GGA GCC AGC CCG CTC CAC TGG GCC              977
Ile His Ser Lys Asp Pro Arg Tyr Gly Ala Ser Pro Leu His Trp Ala
    280                 285                 290

AAG AAT GCC GAG ATG GCC CGG ATG CTG CTG AAG CGG GGA TGT GAT GTG             1025
Lys Asn Ala Glu Met Ala Arg Met Leu Leu Lys Arg Gly Cys Asp Val
295                 300                 305                 310

GAC AGC ACA AGC GCT GCG GGG AAC ACA GCC CTG CAT GTG GCA GTG ATG             1073
Asp Ser Thr Ser Ala Ala Gly Asn Thr Ala Leu His Val Ala Val Met
                315                 320                 325

CGG AAC CGC TTT GAC TGC GTC ATG GTG CTG CTG ACC TAC GGG GCC AAC             1121
Arg Asn Arg Phe Asp Cys Val Met Val Leu Leu Thr Tyr Gly Ala Asn
                330                 335                 340

GCA GGC ACC CCA GGG GAG CAT GGG AAC ACG CCG CTG CAC CTG GCC ATC             1169
Ala Gly Thr Pro Gly Glu His Gly Asn Thr Pro Leu His Leu Ala Ile
        345                 350                 355

TCG AAA GAT AAC ATG GAG ATG ATC AAA GCC CTC ATT GTA TTT GGG GCA             1217
Ser Lys Asp Asn Met Glu Met Ile Lys Ala Leu Ile Val Phe Gly Ala
    360                 365                 370

GAA GTG GAT ACC CCA AAT GAC TTT GGG GAG ACT CCT GCC TTC ATG GCC             1265
Glu Val Asp Thr Pro Asn Asp Phe Gly Glu Thr Pro Ala Phe Met Ala
375                 380                 385                 390

TCC AAG ATC AGC AAA CAG CTT CAG GAC CTC ATG CCC ATC TCC CGA GCC             1313
Ser Lys Ile Ser Lys Gln Leu Gln Asp Leu Met Pro Ile Ser Arg Ala
                395                 400                 405

CGG AAG CCA GCA TTC ATC CTG AGC TCC ATG AGG GAT GAG AAG CGA ATC             1361
Arg Lys Pro Ala Phe Ile Leu Ser Ser Met Arg Asp Glu Lys Arg Ile
                410                 415                 420

CAT GAT CAC CTG CTC TGC CTG GAC GGA GGG GGC GTG AAA GGC CTG GTC             1409
His Asp His Leu Leu Cys Leu Asp Gly Gly Gly Val Lys Gly Leu Val
        425                 430                 435

ATC ATC CAA CTC CTC ATT GCC ATC GAG AAG GCC TCA GGT GTG GCC ACC             1457
Ile Ile Gln Leu Leu Ile Ala Ile Glu Lys Ala Ser Gly Val Ala Thr
    440                 445                 450

AAG GAC CTC TTC GAC TGG GTG GCA GGA ACC AGC ACT GGG GGC ATC CTG             1505
Lys Asp Leu Phe Asp Trp Val Ala Gly Thr Ser Thr Gly Gly Ile Leu
455                 460                 465                 470

GCC CTG GCC ATT CTG CAC AGT AAG TCC ATG GCC TAT ATG CGT GGT GTG             1553
Ala Leu Ala Ile Leu His Ser Lys Ser Met Ala Tyr Met Arg Gly Val
                475                 480                 485

TAC TTC CGT ATG AAA GAT GAG GTG TTT CGG GGC TCA CGG CCC TAT GAG             1601
Tyr Phe Arg Met Lys Asp Glu Val Phe Arg Gly Ser Arg Pro Tyr Glu
                490                 495                 500
```

```
TCT GGA CCC CTG GAG GAG TTC CTG AAG CGG GAG TTT GGG GAG CAC ACC       1649
Ser Gly Pro Leu Glu Glu Phe Leu Lys Arg Glu Phe Gly Glu His Thr
        505                 510                 515

AAG ATG ACA GAT GTC AAA AAA CCC AAG GTG ATG CTC ACA GGG ACA CTG       1697
Lys Met Thr Asp Val Lys Lys Pro Lys Val Met Leu Thr Gly Thr Leu
520                 525                 530

TCT GAC CGG CAG CCA GCA GAG CTC CAC CTG TTC CGC AAT TAC GAT GCT       1745
Ser Asp Arg Gln Pro Ala Glu Leu His Leu Phe Arg Asn Tyr Asp Ala
535                 540                 545                 550

CCA GAG GTC ATT CGG GAA CCT CGC TTC AAC CAA AAC ATT AAC CTG AAG       1793
Pro Glu Val Ile Arg Glu Pro Arg Phe Asn Gln Asn Ile Asn Leu Lys
                555                 560                 565

CCG CCA ACT CAG CCT GCA GAC CAA CTG GTA TGG CGA GCA GCC CGG AGC       1841
Pro Pro Thr Gln Pro Ala Asp Gln Leu Val Trp Arg Ala Ala Arg Ser
        570                 575                 580

AGT GGG GCA GCC CCA ACC TAC TTC CGG CCC AAT GGA CGT TTC CTG GAT       1889
Ser Gly Ala Ala Pro Thr Tyr Phe Arg Pro Asn Gly Arg Phe Leu Asp
                585                 590                 595

GGT GGG CTG CTG GCC AAC AAC CCC ACA CTA GAT GCC ATG ACT GAA ATC       1937
Gly Gly Leu Leu Ala Asn Asn Pro Thr Leu Asp Ala Met Thr Glu Ile
600                 605                 610

CAT GAA TAC AAT CAG GAC ATG ATC CGC AAG GGC CAA GGC AAC AAG GTG       1985
His Glu Tyr Asn Gln Asp Met Ile Arg Lys Gly Gln Gly Asn Lys Val
615                 620                 625                 630

AAG AAA CTC TCC ATA GTC GTC TCT CTG GGG ACA GGA AGG TCC CCT CAA       2033
Lys Lys Leu Ser Ile Val Val Ser Leu Gly Thr Gly Arg Ser Pro Gln
                635                 640                 645

GTG CCC GTA ACC TGT GTA GAT GTC TTC CGC CCC AGC AAC CCC TGG GAA       2081
Val Pro Val Thr Cys Val Asp Val Phe Arg Pro Ser Asn Pro Trp Glu
        650                 655                 660

CTG GCT AAG ACT GTT TTT GGA GCC AAG GAA CTG GGC AAG ATG GTG GTA       2129
Leu Ala Lys Thr Val Phe Gly Ala Lys Glu Leu Gly Lys Met Val Val
                665                 670                 675

GAC TGT TGC ACA GAT CCA GAT GGT CGG GCT GTG GAC CGG GCC CGG GCC       2177
Asp Cys Cys Thr Asp Pro Asp Gly Arg Ala Val Asp Arg Ala Arg Ala
680                 685                 690

TGG AGC GAG ATG GTT GGC ATC CAG TAC TTC AGA CTG AAC CCC CAA CTA       2225
Trp Ser Glu Met Val Gly Ile Gln Tyr Phe Arg Leu Asn Pro Gln Leu
695                 700                 705                 710

GGA TCA GAC ATC ATG CTG GAT GAG GTC AAT GAT GCA GTG CTG GTT AAT       2273
Gly Ser Asp Ile Met Leu Asp Glu Val Asn Asp Ala Val Leu Val Asn
                715                 720                 725

GCC CTC TGG GAG ACA GAA GTC TAC ATC TAT GAG CAC CGG GAG GAG TTC       2321
Ala Leu Trp Glu Thr Glu Val Tyr Ile Tyr Glu His Arg Glu Glu Phe
        730                 735                 740

CAG AAG CTT GTC CAA ATG CTG CTG TCG CCC T GAGCTCCAGG CCCTGCTGGC       2372
Gln Lys Leu Val Gln Met Leu Leu Ser Pro
        745                 750

AGGGGTGCGC CAGGCTACCC AGCACACTGG GGGCCAAGCT GGGCCAGGCG GCTGTGTCTA    2432

CCTGAGGACT GGGGCTCAGA GCACAAACAG GTTCCCACAA GGCACCTCTC CTGACCCATC    2492

TGCACTTTGC CACTCTAGGC TGAAAGCCCA GAGTTCCCCT CAGCCCCTTT ATGTGACTGT    2552

GAAGGACAAC TGGCTCCATC AACTGCCCTA AATATCAGTG AGATCAACAC TAAGGTGTCC    2612

AGTGTACCCA GAGGGTTCTT CCAGGGTCCA TGGCCACCAA AGCCCACCCC TTCTTTCCAC    2672

TTCCTGAAGT CAGTGTCTAC AGAAATGGAG TTCCACCCCA TCATCAGGTG AAATCCAGGC    2732

TATTGAAATC CAGTCTGTTC GACTTTGCCC CTCTGCACCT GCCAATCACC CCACCCCTGC    2792

AGCCACCCCA CCTTAAGAGT CCTCCCAGCT CTCAAAGGTC AATCCTGTGC ATGTACTCTT    2852
```

CTCTGGAAGG AGAGTGGGGA GGGGTTCAAG GCCACCTCAA CTGTGAAATA AATGGGTCTA 2912

GACTCAAAAA AAAAAAGTCG ACG 2935

(2) INFORMATION FOR SEQ ID NO: 2:

(i) SEQUENCE CHARACTERISTICS:
        (A) LENGTH: 752 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gln Phe Phe Gly Arg Leu Val Asn Thr Leu Ser Ser Val Thr Asn
 1               5                  10                  15

Leu Phe Ser Asn Pro Phe Arg Val Lys Glu Ile Ser Val Ala Asp Tyr
             20                  25                  30

Thr Ser His Glu Arg Val Arg Glu Glu Gly Gln Leu Ile Leu Phe Gln
         35                  40                  45

Asn Ala Ser Asn Arg Thr Trp Asp Cys Ile Leu Val Ser Pro Arg Asn
 50                  55                  60

Pro His Ser Gly Phe Arg Leu Phe Gln Leu Glu Ser Glu Ala Asp Ala
 65                  70                  75                  80

Leu Val Asn Phe Gln Gln Phe Ser Ser Gln Leu Pro Pro Phe Tyr Glu
                 85                  90                  95

Ser Ser Val Gln Val Leu His Val Glu Val Leu Gln His Leu Ser Asp
             100                 105                 110

Leu Ile Arg Ser His Pro Ser Trp Thr Val Thr His Leu Ala Val Glu
         115                 120                 125

Leu Gly Ile Arg Glu Cys Phe His His Ser Arg Ile Ile Ser Cys Ala
130                 135                 140

Asn Ser Thr Glu Asn Glu Gly Cys Thr Pro Leu His Leu Ala Cys
145                 150                 155                 160

Arg Lys Gly Asp Ser Glu Ile Leu Val Glu Leu Val Gln Tyr Cys His
                165                 170                 175

Ala Gln Met Asp Val Thr Asp Asn Lys Gly Glu Thr Ala Phe His Tyr
            180                 185                 190

Ala Val Gln Gly Asp Asn Ser Gln Val Leu Gln Leu Leu Gly Lys Asn
        195                 200                 205

Ala Ser Ala Gly Leu Asn Gln Val Asn Lys Gln Gly Leu Thr Pro Leu
210                 215                 220

His Leu Ala Cys Gln Met Gly Lys Gln Glu Met Val Arg Val Leu Leu
225                 230                 235                 240

Leu Cys Asn Ala Arg Cys Asn Val Met Gly Pro Ser Gly Phe Pro Ile
                245                 250                 255

His Thr Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
        275                 280                 285

Ser Pro Leu His Trp Ala Lys Asn Ala Glu Met Ala Arg Met Leu Leu
    290                 295                 300

Lys Arg Gly Cys Asp Val Asp Ser Thr Ser Ala Ala Gly Asn Thr Ala
305                 310                 315                 320

Leu His Val Ala Val Met Arg Asn Arg Phe Asp Cys Val Met Val Leu
                325                 330                 335
```

-continued

```
Leu Thr Tyr Gly Ala Asn Ala Gly Thr Pro Gly Glu His Gly Asn Thr
            340                 345                 350

Pro Leu His Leu Ala Ile Ser Lys Asp Asn Met Glu Met Ile Lys Ala
            355                 360                 365

Leu Ile Val Phe Gly Ala Glu Val Asp Thr Pro Asn Asp Phe Gly Glu
            370                 375                 380

Thr Pro Ala Phe Met Ala Ser Lys Ile Ser Lys Gln Leu Gln Asp Leu
385                         390                 395                 400

Met Pro Ile Ser Arg Ala Arg Lys Pro Ala Phe Ile Leu Ser Ser Met
                    405                 410                 415

Arg Asp Glu Lys Arg Ile His Asp His Leu Leu Cys Leu Asp Gly Gly
                    420                 425                 430

Gly Val Lys Gly Leu Val Ile Ile Gln Leu Leu Ile Ala Ile Glu Lys
            435                 440                 445

Ala Ser Gly Val Ala Thr Lys Asp Leu Phe Asp Trp Val Ala Gly Thr
            450                 455                 460

Ser Thr Gly Gly Ile Leu Ala Leu Ala Ile Leu His Ser Lys Ser Met
465                 470                 475                 480

Ala Tyr Met Arg Gly Val Tyr Phe Arg Met Lys Asp Glu Val Phe Arg
                    485                 490                 495

Gly Ser Arg Pro Tyr Glu Ser Gly Pro Leu Glu Glu Phe Leu Lys Arg
                    500                 505                 510

Glu Phe Gly Glu His Thr Lys Met Thr Asp Val Lys Lys Pro Lys Val
            515                 520                 525

Met Leu Thr Gly Thr Leu Ser Asp Arg Gln Pro Ala Glu Leu His Leu
            530                 535                 540

Phe Arg Asn Tyr Asp Ala Pro Glu Val Ile Arg Glu Pro Arg Phe Asn
545                 550                 555                 560

Gln Asn Ile Asn Leu Lys Pro Pro Thr Gln Pro Ala Asp Gln Leu Val
                    565                 570                 575

Trp Arg Ala Ala Arg Ser Ser Gly Ala Ala Pro Thr Tyr Phe Arg Pro
                    580                 585                 590

Asn Gly Arg Phe Leu Asp Gly Gly Leu Leu Ala Asn Asn Pro Thr Leu
            595                 600                 605

Asp Ala Met Thr Glu Ile His Glu Tyr Asn Gln Asp Met Ile Arg Lys
            610                 615                 620

Gly Gln Gly Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
                    645                 650                 655

Pro Ser Asn Pro Trp Glu Leu Ala Lys Thr Val Phe Gly Ala Lys Glu
                    660                 665                 670

Leu Gly Lys Met Val Val Asp Cys Cys Thr Asp Pro Asp Gly Arg Ala
            675                 680                 685

Val Asp Arg Ala Arg Ala Trp Ser Glu Met Val Gly Ile Gln Tyr Phe
            690                 695                 700

Arg Leu Asn Pro Gln Leu Gly Ser Asp Ile Met Leu Asp Glu Val Asn
705                 710                 715                 720

Asp Ala Val Leu Val Asn Ala Leu Trp Glu Thr Glu Val Tyr Ile Tyr
                    725                 730                 735

Glu His Arg Glu Glu Phe Gln Lys Leu Val Gln Met Leu Leu Ser Pro
            740                 745                 750
```

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:3:

```
Asn Pro His Ser Gly Phe Arg
1               5
```

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:4:

```
Xaa Ala Ser Xaa Gly Leu Asn Gln Val Asn Lys
1               5                   10
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:5:

```
Tyr Gly Ala Ser Pro Leu His Xaa Ala Lys
1               5                   10
```

(2) INFORMATION FOR SEQ ID NO:6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:6:

```
Asp Asn Met Glu Met Ile Lys
1               5
```

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single

```
            (D) TOPOLOGY: linear (ii) MOLECULE TYPE: peptide (iii) HYPOTHETICAL: NO (xi) SEQUENCE DESCRIPTION: SEQ ID NO:7:

Gly Val Tyr Phe Arg
1               5

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:8:

Met Lys Asp Glu Val Phe Arg
1               5

(2) INFORMATION FOR SEQ ID NO:9:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:9:

Glu Phe Gly Glu His Thr Lys
1               5

(2) INFORMATION FOR SEQ ID NO:10:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:10:

Val Met Leu Thr Gly Thr Leu Ser Asp Arg
1               5                   10

(2) INFORMATION FOR SEQ ID NO:11:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:11:
```

```
Xaa Tyr Asp Ala Pro Glu Val Ile Arg
1               5
```

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:12:

```
Phe Asn Gln Asn Ile Asn Leu Lys Pro Pro Thr Gln Pro Ala
1               5                   10
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:13:

```
Xaa Xaa Gly Ala Ala Pro Thr Tyr Phe Arg Pro
1               5                   10
```

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:14:

```
Thr Val Phe Gly Ala Lys
1               5
```

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:15:

```
Xaa Trp Ser Glu Met Val Gly Ile Gln Tyr Phe Arg
1               5                   10
```

(2) INFORMATION FOR SEQ ID NO:16:

(i) SEQUENCE CHARACTERISTICS:
    (A) LENGTH: 2012 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 43..1224

(xi) SEQUENCE DESCRIPTION: SEQ ID NO:16:

```
GAATTCCGGG ACGGTGGGGC CTCCCCACCT GCCCCGCAGA AG ATG CAG TTC TTT            54
                                              Met Gln Phe Phe
                                               1

GGC CGC CTG GTC AAT ACC TTC AGT GGC GTC ACC AAC TTG TTC TCT AAC           102
Gly Arg Leu Val Asn Thr Phe Ser Gly Val Thr Asn Leu Phe Ser Asn
  5                  10                  15                  20

CCA TTC CGG GTG AAG GAG GTG GCT GTG GCC GAC TAC ACC TCG AGT GAC           150
Pro Phe Arg Val Lys Glu Val Ala Val Ala Asp Tyr Thr Ser Ser Asp
                 25                  30                  35

CGA GTT CGG GAG GAA GGG CAG CTG ATT CTG TTC CAG AAC ACT CCC AAC           198
Arg Val Arg Glu Glu Gly Gln Leu Ile Leu Phe Gln Asn Thr Pro Asn
             40                  45                  50

CGC ACC TGG GAC TGC GTC CTG GTC AAC CCC AGG AAC TCA CAG AGT GGA           246
Arg Thr Trp Asp Cys Val Leu Val Asn Pro Arg Asn Ser Gln Ser Gly
         55                  60                  65

TTC CGA CTC TTC CAG CTG GAG TTG GAG GCT GAC GCC CTA GTG AAT TTC           294
Phe Arg Leu Phe Gln Leu Glu Leu Glu Ala Asp Ala Leu Val Asn Phe
     70                  75                  80

CAT CAG TAT TCT TCC CAG CTG CTA CCC TTC TAT GAG AGC TCC CCT CAG           342
His Gln Tyr Ser Ser Gln Leu Leu Pro Phe Tyr Glu Ser Ser Pro Gln
 85                  90                  95                 100

GTC CTG CAC ACT GAG GTC CTG CAG CAC CTG ACC GAC CTC ATC CGT AAC           390
Val Leu His Thr Glu Val Leu Gln His Leu Thr Asp Leu Ile Arg Asn
                105                 110                 115

CAC CCC AGC TGG TCA GTG GCC CAC CTG GCT GTG GAG CTA GGG ATC CGC           438
His Pro Ser Trp Ser Val Ala His Leu Ala Val Glu Leu Gly Ile Arg
            120                 125                 130

GAG TGC TTC CAT CAC AGC CGT ATC ATC AGC TGT GCC AAT TGC GCG GAG           486
Glu Cys Phe His His Ser Arg Ile Ile Ser Cys Ala Asn Cys Ala Glu
        135                 140                 145

AAC GAG GAG GGC TGC ACA CCC CTG CAC CTG GCC TGC CGC AAG GGT GAT           534
Asn Glu Glu Gly Cys Thr Pro Leu His Leu Ala Cys Arg Lys Gly Asp
    150                 155                 160

GGG GAG ATC CTG GTG GAG CTG GTG CAG TAC TGC CAC ACT CAG ATG GAT           582
Gly Glu Ile Leu Val Glu Leu Val Gln Tyr Cys His Thr Gln Met Asp
165                 170                 175                 180

GTC ACC GAC TAC AAG GGA GAG ACC GTC TTC CAT TAT GCT GTC CAG GGT           630
Val Thr Asp Tyr Lys Gly Glu Thr Val Phe His Tyr Ala Val Gln Gly
                185                 190                 195

GAC AAT TCT CAG GTG CTG CAG CTC CTT GGA AGG AAC GCA GTG GCT GGC           678
Asp Asn Ser Gln Val Leu Gln Leu Leu Gly Arg Asn Ala Val Ala Gly
            200                 205                 210

CTG AAC CAG GTG AAT AAC CAA GGG CTG ACC CCG CTG CAC CTG GCC TGC           726
Leu Asn Gln Val Asn Asn Gln Gly Leu Thr Pro Leu His Leu Ala Cys
        215                 220                 225

CAG CTG GGG AAG CAG GAG ATG GTC CGC GTG CTG CTG CTG TGC AAT GCT           774
Gln Leu Gly Lys Gln Glu Met Val Arg Val Leu Leu Leu Cys Asn Ala
    230                 235                 240
```

```
CGG TGC AAC ATC ATG GGC CCC AAC GGC TAC CCC ATC CAC TCG GCC ATG      822
Arg Cys Asn Ile Met Gly Pro Asn Gly Tyr Pro Ile His Ser Ala Met
245                 250                 255                 260

AAG TTC TCT CAG AAG GGG TGT GCG GAG ATG ATC ATC AGC ATG GAC AGC      870
Lys Phe Ser Gln Lys Gly Cys Ala Glu Met Ile Ile Ser Met Asp Ser
                265                 270                 275

AGC CAG ATC CAC AGC AAA GAC CCC CGT TAC GGA GCC AGC CCC CTC CAC      918
Ser Gln Ile His Ser Lys Asp Pro Arg Tyr Gly Ala Ser Pro Leu His
            280                 285                 290

TGG GCC AAG AAC GCA GAG ATG GCC CGC ATG CTG CTG AAA CGG GGC TGC      966
Trp Ala Lys Asn Ala Glu Met Ala Arg Met Leu Leu Lys Arg Gly Cys
        295                 300                 305

AAC GTG AAC AGC ACC AGC TCC GCG GGG AAC ACG GCC CTG CAC GTG GGG     1014
Asn Val Asn Ser Thr Ser Ser Ala Gly Asn Thr Ala Leu His Val Gly
    310                 315                 320

GTG ATG CGC AAC CGC TTC GAC TGT GCC ATA GTG CTG CTG ACC CAC GGG     1062
Val Met Arg Asn Arg Phe Asp Cys Ala Ile Val Leu Leu Thr His Gly
325                 330                 335                 340

GCC AAC GCG GAT GCC CGC GGA GAG CAC GGC AAC ACC CCG CTG CAC CTG     1110
Ala Asn Ala Asp Ala Arg Gly Glu His Gly Asn Thr Pro Leu His Leu
                345                 350                 355

GCC ATG TCG AAA GAC AAC GTG GAG ATG ATC AAG GCC CTC ATC GTG TTC     1158
Ala Met Ser Lys Asp Asn Val Glu Met Ile Lys Ala Leu Ile Val Phe
            360                 365                 370

GGA GCA GAA GTG GAC ACC CCG AAT GAC TTT GGG GAG ACT CCT ACA TTC     1206
Gly Ala Glu Val Asp Thr Pro Asn Asp Phe Gly Glu Thr Pro Thr Phe
        375                 380                 385

CTA GCC TCC AAA ATC GGC AGACTTGTCA CCAGGAAGGC GATCTTGACT             1254
Leu Ala Ser Lys Ile Gly
    390

CTGCTGAGAA CCGTGGGGGC CGAATACTGC TTCCCACCCA TCCACGGGGT CCCCGCGGAG   1314

CAGGGCTCTG CAGCGCCACA TCATCCCTTC TCCCTGGAAA GAGCTCAGCC CCCACCGATC   1374

AGCCTAAACA ACCTAGGCAG TCACCCAAGC CAGGCCGGAT GGTGGGCCTG GGTGCGGCG    1434

TCAGATGGGT AACGCCCTGG GCCTGGAGAG GCCACCGAGC CTAGCCATGC GGCATTAGCT   1494

CTAGCTCTCA CTCCCTAATC CGTCCTTCTT AGCTGCGCAC ACACCACACG CCCCCTCCCC   1554

TGCACCCTGT CCCCGGCCTC TCTCAGCCAC TCTTCTGCTT CCCTTGTTCA CTGTGCAGCC   1614

GTGTGCCCTG GGGAGGGGGA GACACCGCTT CGCAGCCCTC GGTTCTGCTT TGCTGCTTCT   1674

AGACTCTGCA CAGTGGTGGG GGGCTGTCAG AGTTGGGGTC ACGCGGGCTG CTGCACCAGG   1734

CACCTGGGGA CTGGGCTGCT TGTCAGGAGG GGCAGCTAGT CAGTTGGGTG GACGTCGGGC   1794

AGGCCTTGGA CACAAAGGAA GACATGGACA GAGTGGATGG TGGGCCTGAT CCCGGAGGCC   1854

ACTGGGATTT CCAGACCTGG GATCAGGACG AGGGATGTCT CCTTTCATCC ATGGACTTAA   1914

ACCCCGAGGA ACGTCCTGAC TCAGCCTTTT GACTAAATGA CCTTGGGTGA ATTATGGACC   1974

CTCTTAGAGC CTCACCTGTC AATAGGGAAT AAGAATTC                           2012

(2) INFORMATION FOR SEQ ID NO:17:

(i) SEQUENCE CHARACTERISTICS:
        (A) LENGTH: 394 amino acids
        (B) TYPE: amino acid
        (D) TOPOLOGY: linear (ii) MOLECULE TYPE: protein (xi) SEQUENCE DESCRIPTION: SEQ ID NO:17:
```

-continued

```
Met Gln Phe Phe Gly Arg Leu Val Asn Thr Phe Ser Gly Val Thr Asn
 1               5                  10                  15

Leu Phe Ser Asn Pro Phe Arg Val Lys Glu Val Ala Val Ala Asp Tyr
                 20                  25                  30

Thr Ser Ser Asp Arg Val Arg Glu Glu Gly Gln Leu Ile Leu Phe Gln
             35                  40                  45

Asn Thr Pro Asn Arg Thr Trp Asp Cys Val Leu Val Asn Pro Arg Asn
         50                  55                  60

Ser Gln Ser Gly Phe Arg Leu Phe Gln Leu Glu Leu Glu Ala Asp Ala
 65                  70                  75                  80

Leu Val Asn Phe His Gln Tyr Ser Ser Gln Leu Leu Pro Phe Tyr Glu
                 85                  90                  95

Ser Ser Pro Gln Val Leu His Thr Glu Val Leu Gln His Leu Thr Asp
                 100                 105                 110

Leu Ile Arg Asn His Pro Ser Trp Ser Val Ala His Leu Ala Val Glu
                 115                 120                 125

Leu Gly Ile Arg Glu Cys Phe His His Ser Arg Ile Ile Ser Cys Ala
     130                 135                 140

Asn Cys Ala Glu Asn Glu Gly Cys Thr Pro Leu His Leu Ala Cys
145                 150                 155                 160

Arg Lys Gly Asp Gly Glu Ile Leu Val Glu Leu Val Gln Tyr Cys His
                 165                 170                 175

Thr Gln Met Asp Val Thr Asp Tyr Lys Gly Glu Thr Val Phe His Tyr
                 180                 185                 190

Ala Val Gln Gly Asp Asn Ser Gln Val Leu Gln Leu Leu Gly Arg Asn
                 195                 200                 205

Ala Val Ala Gly Leu Asn Gln Val Asn Asn Gln Gly Leu Thr Pro Leu
     210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                 245                 250                 255

His Ser Ala Met Lys Phe Ser Gln Lys Gly Cys Ala Glu Met Ile Ile
                 260                 265                 270

Ser Met Asp Ser Ser Gln Ile His Ser Lys Asp Pro Arg Tyr Gly Ala
                 275                 280                 285

Ser Pro Leu His Trp Ala Lys Asn Ala Glu Met Ala Arg Met Leu Leu
     290                 295                 300

Lys Arg Gly Cys Asn Val Asn Ser Thr Ser Ser Ala Gly Asn Thr Ala
305                 310                 315                 320

Leu His Val Gly Val Met Arg Asn Arg Phe Asp Cys Ala Ile Val Leu
                 325                 330                 335

Leu Thr His Gly Ala Asn Ala Asp Ala Arg Gly Glu His Gly Asn Thr
                 340                 345                 350

Pro Leu His Leu Ala Met Ser Lys Asp Asn Val Glu Met Ile Lys Ala
                 355                 360                 365

Leu Ile Val Phe Gly Ala Glu Val Asp Thr Pro Asn Asp Phe Gly Glu
     370                 375                 380

Thr Pro Thr Phe Leu Ala Ser Lys Ile Gly
385                 390
```

(2) INFORMATION FOR SEQ ID NO:18:

(i) SEQUENCE CHARACTERISTICS:

(A) LENGTH: 1277 base pairs
(B) TYPE: nucleic acid
(C) STRANDEDNESS: double
(D) TOPOLOGY: linear (ii) MOLECULE TYPE: cDNA (iii) HYPOTHETICAL: NO (ix) FEATURE:
(A) NAME/KEY: CDS
(B) LOCATION: 396..1271

(xi) SEQUENCE DESCRIPTION: SEQ ID NO:18:

```
GAATTCTTAG GCCCCAGGTG GTTATTGCAG CATCGGCTCC GATGCAAGAA GAAGCACTTT      60

GTCTGAAGAG GACACGCAAG GGTATTCATG CCTTGGGGTT TCAAGAGGAA GAGATTGAGG     120

GGAACCTGGG AGCTGGCTGG GCAGGGTGGG GAGCCCTTCC CAGAGCAGTG GGCCCCCCTT     180

TCCACTCCAG CCCATTTCTC TCCTGTGGCC TGTGGCTCAG CTTTCTCCTG GACAGAGTC      240

CTTCCTGTGG GGAAGGGACA GATGACAGGG GGAGTGGGGG GATGAGGGCG TGGCCGTGGG     300

CGAGGCACAG CCCAGGTTTG ATCTAGGGAC CTCTGGGGTA GCAGGGCTTG GGACCCACC      360

TGACCACAGC ATGCCCTGCT CTGTGCCTCA CAGAA CTA CAG GAT CTC ATG CAC        413
                                         Leu Gln Asp Leu Met His
                                         1               5

ATC TCA CGG GCC CGG AAG CCA GCG TTC ATC CTG GGC TCC ATG AGG GAC       461
Ile Ser Arg Ala Arg Lys Pro Ala Phe Ile Leu Gly Ser Met Arg Asp
            10                  15                  20

GAG AAG CGG ACC CAC GAC CAC CTG CTG TGC CTG GAT GGA GGA GGA GTG       509
Glu Lys Arg Thr His Asp His Leu Leu Cys Leu Asp Gly Gly Gly Val
        25                  30                  35

AAA GGC CTC ATC ATC ATC CAG CTC CTC ATC GCC ATC GAG AAG GCC TCG       557
Lys Gly Leu Ile Ile Ile Gln Leu Leu Ile Ala Ile Glu Lys Ala Ser
    40                  45                  50

GGT GTG GCC ACC AAG GAC CTG TTT GAC TGG GTG GCG GGC ACC AGC ACT       605
Gly Val Ala Thr Lys Asp Leu Phe Asp Trp Val Ala Gly Thr Ser Thr
55                  60                  65                  70

GGA GGC ATC CTG GCC CTG GCC ATT CTG CAC AGT AAG TCC ATG GCC TAC       653
Gly Gly Ile Leu Ala Leu Ala Ile Leu His Ser Lys Ser Met Ala Tyr
                75                  80                  85

ATG CGC GGC ATG TAC TTT CGC ATG AAG GAT GAG GTG TTC CGG GGC TCC       701
Met Arg Gly Met Tyr Phe Arg Met Lys Asp Glu Val Phe Arg Gly Ser
            90                  95                 100

AGG CCC TAC GAG TCG GGG CCC CTG GAG GAG TTC CTG AAG CGG GAG TTT       749
Arg Pro Tyr Glu Ser Gly Pro Leu Glu Glu Phe Leu Lys Arg Glu Phe
        105                 110                 115

GGG GAG CAC ACC AAG ATG ACG GAC GTC AGG AAA CCC AAG GTG ATG CTG       797
Gly Glu His Thr Lys Met Thr Asp Val Arg Lys Pro Lys Val Met Leu
    120                 125                 130

ACA GGG ACA CTG TCT GAC CGG CAG CCG GCT GAA CTC CAC CTC TTC CGG       845
Thr Gly Thr Leu Ser Asp Arg Gln Pro Ala Glu Leu His Leu Phe Arg
135                 140                 145                 150

AAC TAC GAT GCT CCA GAA ACT GTC CGG GAG CCT CGT TTC AAC CAG AAC       893
Asn Tyr Asp Ala Pro Glu Thr Val Arg Glu Pro Arg Phe Asn Gln Asn
                155                 160                 165

GTT AAC CTC AGG CCT CCA GCT CAG CCC TCA GAC CAG CTG GTG TGG CGG       941
Val Asn Leu Arg Pro Pro Ala Gln Pro Ser Asp Gln Leu Val Trp Arg
            170                 175                 180

GCG GCC CGA AGC AGC GGG GCA GCT CCT ACT TAC TTC CGA CCC AAT GGG       989
Ala Ala Arg Ser Ser Gly Ala Ala Pro Thr Tyr Phe Arg Pro Asn Gly
        185                 190                 195
```

```
CGC TTC CTG GAC GGT GGG CTG TTG GCC AAC AAC CCC ACG CTG GAT GCC      1037
Arg Phe Leu Asp Gly Gly Leu Leu Ala Asn Asn Pro Thr Leu Asp Ala
    200                 205                 210

ATG ACC GAG ATC CAT GAG TAC AAT CAG GAC CTG ATC CGC AAG GGT CAG      1085
Met Thr Glu Ile His Glu Tyr Asn Gln Asp Leu Ile Arg Lys Gly Gln
215                 220                 225                 230

GCC AAC AAG GTG AAG AAA CTC TCC ATC GTT GTC TCC CTG GGG ACA GGG      1133
Ala Asn Lys Val Lys Lys Leu Ser Ile Val Val Ser Leu Gly Thr Gly
                235                 240                 245

AGG TCC CCA CAA GTG CCT GTG ACC TGT GTG GAT GTC TTC CGT CCC AGC      1181
Arg Ser Pro Gln Val Pro Val Thr Cys Val Asp Val Phe Arg Pro Ser
            250                 255                 260

AAC CCC TGG GAG CTG GCC AAG ACT GTT TTT GGG GCC AAG GAA CTG GGC      1229
Asn Pro Trp Glu Leu Ala Lys Thr Val Phe Gly Ala Lys Glu Leu Gly
        265                 270                 275

AAG ATG GTG GTG GAC TGT TGC ACG GAT CCA GAC GGG CGG CCG              1271
Lys Met Val Val Asp Cys Cys Thr Asp Pro Asp Gly Arg Pro
    280                 285                 290

GAATTC                                                                1277
```

(2) INFORMATION FOR SEQ ID NO:19:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO:19:

```
Leu Gln Asp Leu Met His Ile Ser Arg Ala Arg Lys Pro Ala Phe Ile
1               5                   10                  15

Leu Gly Ser Met Arg Asp Glu Lys Arg Thr His Asp His Leu Leu Cys
            20                  25                  30

Leu Asp Gly Gly Gly Val Lys Gly Leu Ile Ile Ile Gln Leu Leu Ile
        35                  40                  45

Ala Ile Glu Lys Ala Ser Gly Val Ala Thr Lys Asp Leu Phe Asp Trp
    50                  55                  60

Val Ala Gly Thr Ser Thr Gly Gly Ile Leu Ala Leu Ala Ile Leu His
65                  70                  75                  80

Ser Lys Ser Met Ala Tyr Met Arg Gly Met Tyr Phe Arg Met Lys Asp
                85                  90                  95

Glu Val Phe Arg Gly Ser Arg Pro Tyr Glu Ser Gly Pro Leu Glu Glu
            100                 105                 110

Phe Leu Lys Arg Glu Phe Gly Glu His Thr Lys Met Thr Asp Val Arg
        115                 120                 125

Lys Pro Lys Val Met Leu Thr Gly Thr Leu Ser Asp Arg Gln Pro Ala
130                 135                 140

Glu Leu His Leu Phe Arg Asn Tyr Asp Ala Pro Glu Thr Val Arg Glu
145                 150                 155                 160

Pro Arg Phe Asn Gln Asn Val Asn Leu Arg Pro Ala Gln Pro Ser
                165                 170                 175

Asp Gln Leu Val Trp Arg Ala Ala Arg Ser Ser Gly Ala Ala Pro Thr
            180                 185                 190

Tyr Phe Arg Pro Asn Gly Arg Phe Leu Asp Gly Gly Leu Leu Ala Asn
        195                 200                 205

Asn Pro Thr Leu Asp Ala Met Thr Glu Ile His Glu Tyr Asn Gln Asp
210                 215                 220
```

```
Leu Ile Arg Lys Gly Gln Ala Asn Lys Val Lys Leu Ser Ile Val
225                 230                 235                 240

Val Ser Leu Gly Thr Gly Arg Ser Pro Gln Val Pro Val Thr Cys Val
            245                 250                 255

Asp Val Phe Arg Pro Ser Asn Pro Trp Glu Leu Ala Lys Thr Val Phe
            260                 265                 270

Gly Ala Lys Glu Leu Gly Lys Met Val Val Asp Cys Cys Thr Asp Pro
            275                 280                 285

Asp Gly Arg Pro
    290
```

(2) INFORMATION FOR SEQ ID NO:20:

(i) SEQUENCE CHARACTERISTICS:
        (A) LENGTH: 2109 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 43..2103

(xi) SEQUENCE DESCRIPTION: SEQ ID NO:20:

```
GAATTCCGGG ACGGTGGGGC CTCCCCACCT GCCCCGCAGA AG ATG CAG TTC TTT         54
                                              Met Gln Phe Phe
                                                1

GGC CGC CTG GTC AAT ACC TTC AGT GGC GTC ACC AAC TTG TTC TCT AAC       102
Gly Arg Leu Val Asn Thr Phe Ser Gly Val Thr Asn Leu Phe Ser Asn
  5                  10                  15                  20

CCA TTC CGG GTG AAG GAG GTG GCT GTG GCC GAC TAC ACC TCG AGT GAC       150
Pro Phe Arg Val Lys Glu Val Ala Val Ala Asp Tyr Thr Ser Ser Asp
                 25                  30                  35

CGA GTT CGG GAG GAA GGG CAG CTG ATT CTG TTC CAG AAC ACT CCC AAC       198
Arg Val Arg Glu Glu Gly Gln Leu Ile Leu Phe Gln Asn Thr Pro Asn
             40                  45                  50

CGC ACC TGG GAC TGC GTC CTG GTC AAC CCC AGG AAC TCA CAG AGT GGA       246
Arg Thr Trp Asp Cys Val Leu Val Asn Pro Arg Asn Ser Gln Ser Gly
         55                  60                  65

TTC CGA CTC TTC CAG CTG GAG TTG GAG GCT GAC GCC CTA GTG AAT TTC       294
Phe Arg Leu Phe Gln Leu Glu Leu Glu Ala Asp Ala Leu Val Asn Phe
     70                  75                  80

CAT CAG TAT TCT TCC CAG CTG CTA CCC TTC TAT GAG AGC TCC CCT CAG       342
His Gln Tyr Ser Ser Gln Leu Leu Pro Phe Tyr Glu Ser Ser Pro Gln
 85                  90                  95                 100

GTC CTG CAC ACT GAG GTC CTG CAG CAC CTG ACC GAC CTC ATC CGT AAC       390
Val Leu His Thr Glu Val Leu Gln His Leu Thr Asp Leu Ile Arg Asn
                105                 110                 115

CAC CCC AGC TGG TCA GTG GCC CAC CTG GCT GTG GAG CTA GGG ATC CGC       438
His Pro Ser Trp Ser Val Ala His Leu Ala Val Glu Leu Gly Ile Arg
            120                 125                 130

GAG TGC TTC CAT CAC AGC CGT ATC ATC AGC TGT GCC AAT TGC GCG GAG       486
Glu Cys Phe His His Ser Arg Ile Ile Ser Cys Ala Asn Cys Ala Glu
        135                 140                 145

AAC GAG GAG GGC TGC ACA CCC CTG CAC CTG GCC TGC CGC AAG GGT GAT       534
Asn Glu Glu Gly Cys Thr Pro Leu His Leu Ala Cys Arg Lys Gly Asp
    150                 155                 160
```

```
GGG GAG ATC CTG GTG GAG CTG GTG CAG TAC TGC CAC ACT CAG ATG GAT        582
Gly Glu Ile Leu Val Glu Leu Val Gln Tyr Cys His Thr Gln Met Asp
165             170                 175                 180

GTC ACC GAC TAC AAG GGA GAG ACC GTC TTC CAT TAT GCT GTC CAG GGT        630
Val Thr Asp Tyr Lys Gly Glu Thr Val Phe His Tyr Ala Val Gln Gly
                185                 190                 195

GAC AAT TCT CAG GTG CTG CAG CTC CTT GGA AGG AAC GCA GTG GCT GGC        678
Asp Asn Ser Gln Val Leu Gln Leu Leu Gly Arg Asn Ala Val Ala Gly
            200                 205                 210

CTG AAC CAG GTG AAT AAC CAA GGG CTG ACC CCG CTG CAC CTG GCC TGC        726
Leu Asn Gln Val Asn Asn Gln Gly Leu Thr Pro Leu His Leu Ala Cys
        215                 220                 225

CAG CTG GGG AAG CAG GAG ATG GTC CGC GTG CTG CTG CTG TGC AAT GCT        774
Gln Leu Gly Lys Gln Glu Met Val Arg Val Leu Leu Leu Cys Asn Ala
230                 235                 240

CGG TGC AAC ATC ATG GGC CCC AAC GGC TAC CCC ATC CAC TCG GCC ATG        822
Arg Cys Asn Ile Met Gly Pro Asn Gly Tyr Pro Ile His Ser Ala Met
245                 250                 255                 260

AAG TTC TCT CAG AAG GGG TGT GCG GAG ATG ATC ATC AGC ATG GAC AGC        870
Lys Phe Ser Gln Lys Gly Cys Ala Glu Met Ile Ile Ser Met Asp Ser
                265                 270                 275

AGC CAG ATC CAC AGC AAA GAC CCC CGT TAC GGA GCC AGC CCC CTC CAC        918
Ser Gln Ile His Ser Lys Asp Pro Arg Tyr Gly Ala Ser Pro Leu His
            280                 285                 290

TGG GCC AAG AAC GCA GAG ATG GCC CGC ATG CTG CTG AAA CGG GGC TGC        966
Trp Ala Lys Asn Ala Glu Met Ala Arg Met Leu Leu Lys Arg Gly Cys
        295                 300                 305

AAC GTG AAC AGC ACC AGC TCC GCG GGG AAC ACG GCC CTG CAC GTG GGG       1014
Asn Val Asn Ser Thr Ser Ser Ala Gly Asn Thr Ala Leu His Val Gly
310                 315                 320

GTG ATG CGC AAC CGC TTC GAC TGT GCC ATA GTG CTG CTG ACC CAC GGG       1062
Val Met Arg Asn Arg Phe Asp Cys Ala Ile Val Leu Leu Thr His Gly
325                 330                 335                 340

GCC AAC GCG GAT GCC CGC GGA GAG CAC GGC AAC ACC CCG CTG CAC CTG       1110
Ala Asn Ala Asp Ala Arg Gly Glu His Gly Asn Thr Pro Leu His Leu
                345                 350                 355

GCC ATG TCG AAA GAC AAC GTG GAG ATG ATC AAG GCC CTC ATC GTG TTC       1158
Ala Met Ser Lys Asp Asn Val Glu Met Ile Lys Ala Leu Ile Val Phe
            360                 365                 370

GGA GCA GAA GTG GAC ACC CCG AAT GAC TTT GGG GAG ACT CCT ACA TTC       1206
Gly Ala Glu Val Asp Thr Pro Asn Asp Phe Gly Glu Thr Pro Thr Phe
        375                 380                 385

CTA GCC TCC AAA ATC GGC AAA CTA CAG GAT CTC ATG CAC ATC TCA CGG       1254
Leu Ala Ser Lys Ile Gly Lys Leu Gln Asp Leu Met His Ile Ser Arg
390                 395                 400

GCC CGG AAG CCA GCG TTC ATC CTG GGC TCC ATG AGG GAC GAG AAG CGG       1302
Ala Arg Lys Pro Ala Phe Ile Leu Gly Ser Met Arg Asp Glu Lys Arg
405                 410                 415                 420

ACC CAC GAC CAC CTG CTG TGC CTG GAT GGA GGA GGA GTG AAA GGC CTC       1350
Thr His Asp His Leu Leu Cys Leu Asp Gly Gly Gly Val Lys Gly Leu
                425                 430                 435

ATC ATC ATC CAG CTC CTC ATC GCC ATC GAG AAG GCC TCG GGT GTG GCC       1398
Ile Ile Ile Gln Leu Leu Ile Ala Ile Glu Lys Ala Ser Gly Val Ala
            440                 445                 450

ACC AAG GAC CTG TTT GAC TGG GTG GCG GGC ACC AGC ACT GGA GGC ATC       1446
Thr Lys Asp Leu Phe Asp Trp Val Ala Gly Thr Ser Thr Gly Gly Ile
        455                 460                 465

CTG GCC CTG GCC ATT CTG CAC AGT AAG TCC ATG GCC TAC ATG CGC GGC       1494
Leu Ala Leu Ala Ile Leu His Ser Lys Ser Met Ala Tyr Met Arg Gly
470                 475                 480
```

-continued

```
ATG TAC TTT CGC ATG AAG GAT GAG GTG TTC CGG GGC TCC AGG CCC TAC      1542
Met Tyr Phe Arg Met Lys Asp Glu Val Phe Arg Gly Ser Arg Pro Tyr
485                 490                 495                 500

GAG TCG GGG CCC CTG GAG GAG TTC CTG AAG CGG GAG TTT GGG GAG CAC      1590
Glu Ser Gly Pro Leu Glu Glu Phe Leu Lys Arg Glu Phe Gly Glu His
                505                 510                 515

ACC AAG ATG ACG GAC GTC AGG AAA CCC AAG GTG ATG CTG ACA GGG ACA      1638
Thr Lys Met Thr Asp Val Arg Lys Pro Lys Val Met Leu Thr Gly Thr
            520                 525                 530

CTG TCT GAC CGG CAG CCG GCT GAA CTC CAC CTC TTC CGG AAC TAC GAT      1686
Leu Ser Asp Arg Gln Pro Ala Glu Leu His Leu Phe Arg Asn Tyr Asp
        535                 540                 545

GCT CCA GAA ACT GTC CGG GAG CCT CGT TTC AAC CAG AAC GTT AAC CTC      1734
Ala Pro Glu Thr Val Arg Glu Pro Arg Phe Asn Gln Asn Val Asn Leu
    550                 555                 560

AGG CCT CCA GCT CAG CCC TCA GAC CAG CTG GTG TGG CGG GCG GCC CGA      1782
Arg Pro Pro Ala Gln Pro Ser Asp Gln Leu Val Trp Arg Ala Ala Arg
565                 570                 575                 580

AGC AGC GGG GCA GCT CCT ACT TAC TTC CGA CCC AAT GGG CGC TTC CTG      1830
Ser Ser Gly Ala Ala Pro Thr Tyr Phe Arg Pro Asn Gly Arg Phe Leu
                585                 590                 595

GAC GGT GGG CTG TTG GCC AAC AAC CCC ACG CTG GAT GCC ATG ACC GAG      1878
Asp Gly Gly Leu Leu Ala Asn Asn Pro Thr Leu Asp Ala Met Thr Glu
                    600                 605                 610

ATC CAT GAG TAC AAT CAG GAC CTG ATC CGC AAG GGT CAG GCC AAC AAG      1926
Ile His Glu Tyr Asn Gln Asp Leu Ile Arg Lys Gly Gln Ala Asn Lys
            615                 620                 625

GTG AAG AAA CTC TCC ATC GTT GTC TCC CTG GGG ACA GGG AGG TCC CCA      1974
Val Lys Lys Leu Ser Ile Val Val Ser Leu Gly Thr Gly Arg Ser Pro
        630                 635                 640

CAA GTG CCT GTG ACC TGT GTG GAT GTC TTC CGT CCC AGC AAC CCC TGG      2022
Gln Val Pro Val Thr Cys Val Asp Val Phe Arg Pro Ser Asn Pro Trp
    645                 650                 655                 660

GAG CTG GCC AAG ACT GTT TTT GGG GCC AAG GAA CTG GGC AAG ATG GTG      2070
Glu Leu Ala Lys Thr Val Phe Gly Ala Lys Glu Leu Gly Lys Met Val
                665                 670                 675

GTG GAC TGT TGC ACG GAT CCA GAC GGG CGG CCG GAATTC                   2109
Val Asp Cys Cys Thr Asp Pro Asp Gly Arg Pro
                680                 685
```

(2) INFORMATION FOR SEQ ID NO:21:

(i) SEQUENCE CHARACTERISTICS:
        (A) LENGTH: 687 amino acids
        (B) TYPE: amino acid
        (D) TOPOLOGY: linear (ii) MOLECULE TYPE: protein (xi) SEQUENCE DESCRIPTION: SEQ ID NO:21:

```
Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Glu Ala Asp Ala
65                  70                  75                  80
```

```
Leu Val Asn Phe His Gln Tyr Ser Ser Gln Leu Leu Pro Phe Tyr Glu
                85                  90                  95
Ser Ser Pro Gln Val Leu His Thr Glu Val Leu Gln His Leu Thr Asp
            100                 105                 110
Leu Ile Arg Asn His Pro Ser Trp Ser Val Ala His Leu Ala Val Glu
        115                 120                 125
Leu Gly Ile Arg Glu Cys Phe His His Ser Arg Ile Ile Ser Cys Ala
    130                 135                 140
Asn Cys Ala Glu Asn Glu Glu Gly Cys Thr Pro Leu His Leu Ala Cys
145                 150                 155                 160
Arg Lys Gly Asp Gly Glu Ile Leu Val Glu Leu Val Gln Tyr Cys His
                165                 170                 175
Thr Gln Met Asp Val Thr Asp Tyr Lys Gly Glu Thr Val Phe His Tyr
            180                 185                 190
Ala Val Gln Gly Asp Asn Ser Gln Val Leu Gln Leu Leu Gly Arg Asn
        195                 200                 205
Ala Val Ala Gly Leu Asn Gln Val Asn Asn Gln Gly Leu Thr Pro Leu
    210                 215                 220
His Leu Ala Cys Gln Leu Gly Lys Gln Glu Met Val Arg Val Leu Leu
225                 230                 235                 240
Leu Cys Asn Ala Arg Cys Asn Ile Met Gly Pro Asn Gly Tyr Pro Ile
                245                 250                 255
His Ser Ala Met Lys Phe Ser Gln Lys Gly Cys Ala Glu Met Ile Ile
            260                 265                 270
Ser Met Asp Ser Ser Gln Ile His Ser Lys Asp Pro Arg Tyr Gly Ala
        275                 280                 285
Ser Pro Leu His Trp Ala Lys Asn Ala Glu Met Ala Arg Met Leu Leu
    290                 295                 300
Lys Arg Gly Cys Asn Val Asn Ser Thr Ser Ser Ala Gly Asn Thr Ala
305                 310                 315                 320
Leu His Val Gly Val Met Arg Asn Arg Phe Asp Cys Ala Ile Val Leu
                325                 330                 335
Leu Thr His Gly Ala Asn Ala Asp Ala Arg Gly Glu His Gly Asn Thr
            340                 345                 350
Pro Leu His Leu Ala Met Ser Lys Asp Asn Val Glu Met Ile Lys Ala
        355                 360                 365
Leu Ile Val Phe Gly Ala Glu Val Asp Thr Pro Asn Asp Phe Gly Glu
    370                 375                 380
Thr Pro Thr Phe Leu Ala Ser Lys Ile Gly Lys Leu Gln Asp Leu Met
385                 390                 395                 400
His Ile Ser Arg Ala Arg Lys Pro Ala Phe Ile Leu Gly Ser Met Arg
                405                 410                 415
Asp Glu Lys Arg Thr His Asp His Leu Leu Cys Leu Asp Gly Gly Gly
            420                 425                 430
Val Lys Gly Leu Ile Ile Ile Gln Leu Leu Ile Ala Ile Glu Lys Ala
        435                 440                 445
Ser Gly Val Ala Thr Lys Asp Leu Phe Asp Trp Val Ala Gly Thr Ser
    450                 455                 460
Thr Gly Gly Ile Leu Ala Leu Ala Ile Leu His Ser Lys Ser Met Ala
465                 470                 475                 480
Tyr Met Arg Gly Met Tyr Phe Arg Met Lys Asp Glu Val Phe Arg Gly
                485                 490                 495
```

```
Ser Arg Pro Tyr Glu Ser Gly Pro Leu Glu Glu Phe Leu Lys Arg Glu
            500                 505                 510

Phe Gly Glu His Thr Lys Met Thr Asp Val Arg Lys Pro Lys Val Met
            515                 520                 525

Leu Thr Gly Thr Leu Ser Asp Arg Gln Pro Ala Glu Leu His Leu Phe
            530                 535                 540

Arg Asn Tyr Asp Ala Pro Glu Thr Val Arg Glu Pro Arg Phe Asn Gln
545                 550                 555                 560

Asn Val Asn Leu Arg Pro Pro Ala Gln Pro Ser Asp Gln Leu Val Trp
                565                 570                 575

Arg Ala Ala Arg Ser Ser Gly Ala Ala Pro Thr Tyr Phe Arg Pro Asn
            580                 585                 590

Gly Arg Phe Leu Asp Gly Gly Leu Leu Ala Asn Asn Pro Thr Leu Asp
            595                 600                 605

Ala Met Thr Glu Ile His Glu Tyr Asn Gln Asp Leu Ile Arg Lys Gly
            610                 615                 620

Gln Ala Asn Lys Val Lys Lys Leu Ser Ile Val Ser Leu Gly Thr
625                 630                 635                 640

Gly Arg Ser Pro Gln Val Pro Val Thr Cys Val Asp Val Phe Arg Pro
                645                 650                 655

Ser Asn Pro Trp Glu Leu Ala Lys Thr Val Phe Gly Ala Lys Glu Leu
            660                 665                 670

Gly Lys Met Val Val Asp Cys Cys Thr Asp Pro Asp Gly Arg Pro
            675                 680                 685

(2) INFORMATION FOR SEQ ID NO:22:

(i) SEQUENCE CHARACTERISTICS:
        (A) LENGTH: 2112 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 43..2106

(xi) SEQUENCE DESCRIPTION: SEQ ID NO:22:

GAATTCCGGG ACGGTGGGGC CTCCCCACCT GCCCCGCAGA AG ATG CAG TTC TTT      54
                                              Met Gln Phe Phe
                                                1

GGC CGC CTG GTC AAT ACC TTC AGT GGC GTC ACC AAC TTG TTC TCT AAC   102
Gly Arg Leu Val Asn Thr Phe Ser Gly Val Thr Asn Leu Phe Ser Asn
 5                  10                  15                  20

CCA TTC CGG GTG AAG GAG GTG GCT GTG GCC GAC TAC ACC TCG AGT GAC   150
Pro Phe Arg Val Lys Glu Val Ala Val Ala Asp Tyr Thr Ser Ser Asp
                25                  30                  35

CGA GTT CGG GAG GAA GGG CAG CTG ATT CTG TTC CAG AAC ACT CCC AAC   198
Arg Val Arg Glu Glu Gly Gln Leu Ile Leu Phe Gln Asn Thr Pro Asn
            40                  45                  50

CGC ACC TGG GAC TGC GTC CTG GTC AAC CCC AGG AAC TCA CAG AGT GGA   246
Arg Thr Trp Asp Cys Val Leu Val Asn Pro Arg Asn Ser Gln Ser Gly
        55                  60                  65

TTC CGA CTC TTC CAG CTG GAG TTG GAG GCT GAC GCC CTA GTG AAT TTC   294
Phe Arg Leu Phe Gln Leu Glu Leu Glu Ala Asp Ala Leu Val Asn Phe
    70                  75                  80
```

-continued

```
CAT CAG TAT TCT TCC CAG CTG CTA CCC TTC TAT GAG AGC TCC CCT CAG      342
His Gln Tyr Ser Ser Gln Leu Leu Pro Phe Tyr Glu Ser Ser Pro Gln
 85              90                  95                 100

GTC CTG CAC ACT GAG GTC CTG CAG CAC CTG ACC GAC CTC ATC CGT AAC      390
Val Leu His Thr Glu Val Leu Gln His Leu Thr Asp Leu Ile Arg Asn
             105                 110                 115

CAC CCC AGC TGG TCA GTG GCC CAC CTG GCT GTG GAG CTA GGG ATC CGC      438
His Pro Ser Trp Ser Val Ala His Leu Ala Val Glu Leu Gly Ile Arg
         120                 125                 130

GAG TGC TTC CAT CAC AGC CGT ATC ATC AGC TGT GCC AAT TGC GCG GAG      486
Glu Cys Phe His His Ser Arg Ile Ile Ser Cys Ala Asn Cys Ala Glu
     135                 140                 145

AAC GAG GAG GGC TGC ACA CCC CTG CAC CTG GCC TGC CGC AAG GGT GAT      534
Asn Glu Glu Gly Cys Thr Pro Leu His Leu Ala Cys Arg Lys Gly Asp
 150                 155                 160

GGG GAG ATC CTG GTG GAG CTG GTG CAG TAC TGC CAC ACT CAG ATG GAT      582
Gly Glu Ile Leu Val Glu Leu Val Gln Tyr Cys His Thr Gln Met Asp
165                 170                 175                 180

GTC ACC GAC TAC AAG GGA GAG ACC GTC TTC CAT TAT GCT GTC CAG GGT      630
Val Thr Asp Tyr Lys Gly Glu Thr Val Phe His Tyr Ala Val Gln Gly
             185                 190                 195

GAC AAT TCT CAG GTG CTG CAG CTC CTT GGA AGG AAC GCA GTG GCT GGC      678
Asp Asn Ser Gln Val Leu Gln Leu Leu Gly Arg Asn Ala Val Ala Gly
         200                 205                 210

CTG AAC CAG GTG AAT AAC CAA GGG CTG ACC CCG CTG CAC CTG GCC TGC      726
Leu Asn Gln Val Asn Asn Gln Gly Leu Thr Pro Leu His Leu Ala Cys
     215                 220                 225

CAG CTG GGG AAG CAG GAG ATG GTC CGC GTG CTG CTG CTG TGC AAT GCT      774
Gln Leu Gly Lys Gln Glu Met Val Arg Val Leu Leu Leu Cys Asn Ala
 230                 235                 240

CGG TGC AAC ATC ATG GGC CCC AAC GGC TAC CCC ATC CAC TCG GCC ATG      822
Arg Cys Asn Ile Met Gly Pro Asn Gly Tyr Pro Ile His Ser Ala Met
245                 250                 255                 260

AAG TTC TCT CAG AAG GGG TGT GCG GAG ATG ATC ATC AGC ATG GAC AGC      870
Lys Phe Ser Gln Lys Gly Cys Ala Glu Met Ile Ile Ser Met Asp Ser
             265                 270                 275

AGC CAG ATC CAC AGC AAA GAC CCC CGT TAC GGA GCC AGC CCC CTC CAC      918
Ser Gln Ile His Ser Lys Asp Pro Arg Tyr Gly Ala Ser Pro Leu His
         280                 285                 290

TGG GCC AAG AAC GCA GAG ATG GCC CGC ATG CTG CTG AAA CGG GGC TGC      966
Trp Ala Lys Asn Ala Glu Met Ala Arg Met Leu Leu Lys Arg Gly Cys
     295                 300                 305

AAC GTG AAC AGC ACC AGC TCC GCG GGG AAC ACG GCC CTG CAC GTG GGG     1014
Asn Val Asn Ser Thr Ser Ser Ala Gly Asn Thr Ala Leu His Val Gly
 310                 315                 320

GTG ATG CGC AAC CGC TTC GAC TGT GCC ATA GTG CTG CTG ACC CAC GGG     1062
Val Met Arg Asn Arg Phe Asp Cys Ala Ile Val Leu Leu Thr His Gly
325                 330                 335                 340

GCC AAC GCG GAT GCC CGC GGA GAG CAC GGC AAC ACC CCG CTG CAC CTG     1110
Ala Asn Ala Asp Ala Arg Gly Glu His Gly Asn Thr Pro Leu His Leu
             345                 350                 355

GCC ATG TCG AAA GAC AAC GTG GAG ATG ATC AAG GCC CTC ATC GTG TTC     1158
Ala Met Ser Lys Asp Asn Val Glu Met Ile Lys Ala Leu Ile Val Phe
         360                 365                 370

GGA GCA GAA GTG GAC ACC CCG AAT GAC TTT GGG GAG ACT CCT ACA TTC     1206
Gly Ala Glu Val Asp Thr Pro Asn Asp Phe Gly Glu Thr Pro Thr Phe
     375                 380                 385

CTA GCC TCC AAA ATC GGC AGA CAA CTA CAG GAT CTC ATG CAC ATC TCA     1254
Leu Ala Ser Lys Ile Gly Arg Gln Leu Gln Asp Leu Met His Ile Ser
 390                 395                 400
```

```
CGG GCC CGG AAG CCA GCG TTC ATC CTG GGC TCC ATG AGG GAC GAG AAG      1302
Arg Ala Arg Lys Pro Ala Phe Ile Leu Gly Ser Met Arg Asp Glu Lys
405                 410                 415                 420

CGG ACC CAC GAC CAC CTG CTG TGC CTG GAT GGA GGA GGA GTG AAA GGC      1350
Arg Thr His Asp His Leu Leu Cys Leu Asp Gly Gly Gly Val Lys Gly
                425                 430                 435

CTC ATC ATC ATC CAG CTC CTC ATC GCC ATC GAG AAG GCC TCG GGT GTG      1398
Leu Ile Ile Ile Gln Leu Leu Ile Ala Ile Glu Lys Ala Ser Gly Val
            440                 445                 450

GCC ACC AAG GAC CTG TTT GAC TGG GTG GCG GGC ACC AGC ACT GGA GGC      1446
Ala Thr Lys Asp Leu Phe Asp Trp Val Ala Gly Thr Ser Thr Gly Gly
        455                 460                 465

ATC CTG GCC CTG GCC ATT CTG CAC AGT AAG TCC ATG GCC TAC ATG CGC      1494
Ile Leu Ala Leu Ala Ile Leu His Ser Lys Ser Met Ala Tyr Met Arg
    470                 475                 480

GGC ATG TAC TTT CGC ATG AAG GAT GAG GTG TTC CGG GGC TCC AGG CCC      1542
Gly Met Tyr Phe Arg Met Lys Asp Glu Val Phe Arg Gly Ser Arg Pro
485                 490                 495                 500

TAC GAG TCG GGG CCC CTG GAG GAG TTC CTG AAG CGG GAG TTT GGG GAG      1590
Tyr Glu Ser Gly Pro Leu Glu Glu Phe Leu Lys Arg Glu Phe Gly Glu
                505                 510                 515

CAC ACC AAG ATG ACG GAC GTC AGG AAA CCC AAG GTG ATG CTG ACA GGG      1638
His Thr Lys Met Thr Asp Val Arg Lys Pro Lys Val Met Leu Thr Gly
            520                 525                 530

ACA CTG TCT GAC CGG CAG CCG GCT GAA CTC CAC CTC TTC CGG AAC TAC      1686
Thr Leu Ser Asp Arg Gln Pro Ala Glu Leu His Leu Phe Arg Asn Tyr
        535                 540                 545

GAT GCT CCA GAA ACT GTC CGG GAG CCT CGT TTC AAC CAG AAC GTT AAC      1734
Asp Ala Pro Glu Thr Val Arg Glu Pro Arg Phe Asn Gln Asn Val Asn
    550                 555                 560

CTC AGG CCT CCA GCT CAG CCC TCA GAC CAG CTG GTG TGG CGG GCG GCC      1782
Leu Arg Pro Pro Ala Gln Pro Ser Asp Gln Leu Val Trp Arg Ala Ala
565                 570                 575                 580

CGA AGC AGC GGG GCA GCT CCT ACT TAC TTC CGA CCC AAT GGG CGC TTC      1830
Arg Ser Ser Gly Ala Ala Pro Thr Tyr Phe Arg Pro Asn Gly Arg Phe
                585                 590                 595

CTG GAC GGT GGG CTG TTG GCC AAC AAC CCC ACG CTG GAT GCC ATG ACC      1878
Leu Asp Gly Gly Leu Leu Ala Asn Asn Pro Thr Leu Asp Ala Met Thr
            600                 605                 610

GAG ATC CAT GAG TAC AAT CAG GAC CTG ATC CGC AAG GGT CAG GCC AAC      1926
Glu Ile His Glu Tyr Asn Gln Asp Leu Ile Arg Lys Gly Gln Ala Asn
        615                 620                 625

AAG GTG AAG AAA CTC TCC ATC GTT GTC TCC CTG GGG ACA GGG AGG TCC      1974
Lys Val Lys Lys Leu Ser Ile Val Val Ser Leu Gly Thr Gly Arg Ser
    630                 635                 640

CCA CAA GTG CCT GTG ACC TGT GTG GAT GTC TTC CGT CCC AGC AAC CCC      2022
Pro Gln Val Pro Val Thr Cys Val Asp Val Phe Arg Pro Ser Asn Pro
645                 650                 655                 660

TGG GAG CTG GCC AAG ACT GTT TTT GGG GCC AAG GAA CTG GGC AAG ATG      2070
Trp Glu Leu Ala Lys Thr Val Phe Gly Ala Lys Glu Leu Gly Lys Met
                665                 670                 675

GTG GTG GAC TGT TGC ACG GAT CCA GAC GGG CGG CCG GAATTC               2112
Val Val Asp Cys Cys Thr Asp Pro Asp Gly Arg Pro
            680                 685
```

(2) INFORMATION FOR SEQ ID NO:23:

(i) SEQUENCE CHARACTERISTICS:
        (A) LENGTH: 688 amino acids
        (B) TYPE: amino acid -continued (D) TOPOLOGY: linear (ii) MOLECULE TYPE: protein (xi) SEQUENCE DESCRIPTION: SEQ ID NO:23:

```
Met Gln Phe Phe Gly Arg Leu Val Asn Thr Phe Ser Gly Val Thr Asn
 1               5                  10                  15

Leu Phe Ser Asn Pro Phe Arg Val Lys Glu Val Ala Val Ala Asp Tyr
            20                  25                  30

Thr Ser Ser Asp Arg Val Arg Glu Glu Gly Gln Leu Ile Leu Phe Gln
         35                  40                  45

Asn Thr Pro Asn Arg Thr Trp Asp Cys Val Leu Val Asn Pro Arg Asn
     50                  55                  60

Ser Gln Ser Gly Phe Arg Leu Phe Gln Leu Glu Leu Glu Ala Asp Ala
 65                  70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
        115                 120                 125

Leu Gly Ile Arg Glu Cys Phe His His Ser Arg Ile Ile Ser Cys Ala
    130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Asn Gly Leu Thr Pro Leu
    210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
        275                 280                 285

Ser Pro Leu His Trp Ala Lys Asn Ala Glu Met Ala Arg Met Leu Leu
    290                 295                 300

Lys Arg Gly Cys Asn Val Asn Ser Thr Ser Ala Gly Asn Thr Ala
305                 310                 315                 320

Leu His Val Gly Val Met Arg Asn Arg Phe Asp Cys Ala Ile Val Leu
                325                 330                 335

Leu Thr His Gly Ala Asn Ala Asp Ala Arg Gly Glu His Gly Asn Thr
            340                 345                 350

Pro Leu His Leu Ala Met Ser Lys Asp Asn Val Glu Met Ile Lys Ala
        355                 360                 365

Leu Ile Val Phe Gly Ala Glu Val Asp Thr Pro Asn Asp Phe Gly Glu
    370                 375                 380

Thr Pro Thr Phe Leu Ala Ser Lys Ile Gly Arg Gln Leu Gln Asp Leu
```

```
                385                 390                 395                 400
Met His Ile Ser Arg Ala Arg Lys Pro Ala Phe Ile Leu Gly Ser Met
                405                 410                 415
Arg Asp Glu Lys Arg Thr His Asp His Leu Leu Cys Leu Asp Gly Gly
                420                 425                 430
Gly Val Lys Gly Leu Ile Ile Ile Gln Leu Leu Ile Ala Ile Glu Lys
                435                 440                 445
Ala Ser Gly Val Ala Thr Lys Asp Leu Phe Asp Trp Val Ala Gly Thr
                450                 455                 460
Ser Thr Gly Gly Ile Leu Ala Leu Ala Ile Leu His Ser Lys Ser Met
465                 470                 475                 480
Ala Tyr Met Arg Gly Met Tyr Phe Arg Met Lys Asp Glu Val Phe Arg
                485                 490                 495
Gly Ser Arg Pro Tyr Glu Ser Gly Pro Leu Glu Glu Phe Leu Lys Arg
                500                 505                 510
Glu Phe Gly Glu His Thr Lys Met Thr Asp Val Arg Lys Pro Lys Val
                515                 520                 525
Met Leu Thr Gly Thr Leu Ser Asp Arg Gln Pro Ala Glu Leu His Leu
                530                 535                 540
Phe Arg Asn Tyr Asp Ala Pro Glu Thr Val Arg Glu Pro Arg Phe Asn
545                 550                 555                 560
Gln Asn Val Asn Leu Arg Pro Ala Gln Pro Ser Asp Gln Leu Val
                565                 570                 575
Trp Arg Ala Ala Arg Ser Ser Gly Ala Ala Pro Thr Tyr Phe Arg Pro
                580                 585                 590
Asn Gly Arg Phe Leu Asp Gly Gly Leu Leu Ala Asn Asn Pro Thr Leu
                595                 600                 605
Asp Ala Met Thr Glu Ile His Glu Tyr Asn Gln Asp Leu Ile Arg Lys
                610                 615                 620
Gly Gln Ala Asn Lys Val Lys Lys Leu Ser Ile Val Val Ser Leu Gly
625                 630                 635                 640
Thr Gly Arg Ser Pro Gln Val Pro Val Thr Cys Val Asp Val Phe Arg
                645                 650                 655
Pro Ser Asn Pro Trp Glu Leu Ala Lys Thr Val Phe Gly Ala Lys Glu
                660                 665                 670
Leu Gly Lys Met Val Val Asp Cys Cys Thr Asp Pro Asp Gly Arg Pro
                675                 680                 685
```

(2) INFORMATION FOR SEQ ID NO:24:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: oligonucleotides (iii) HYPOTHETICAL: NO (xi) SEQUENCE DESCRIPTION: SEQ ID NO:24:

CATGGGACCC GCTGGCTTTC C                                  21

(2) INFORMATION FOR SEQ ID NO:25:

(i) SEQUENCE CHARACTERISTICS:
        (A) LENGTH: 22 bases
        (B) TYPE: nucleic acid

```
        (C) STRANDEDNESS: single
        (D) TOPOLOGY: linear (ii) MOLECULE TYPE: oligonucleotides (iii) HYPOTHETICAL: NO (xi) SEQUENCE DESCRIPTION: SEQ ID NO:25:

GGCAGGAACC GCCACTGGGG GC                                                     22
```